US008603476B2

(12) United States Patent
Uehara et al.

(10) Patent No.: US 8,603,476 B2
(45) Date of Patent: Dec. 10, 2013

(54) HUMANIZED ANTI-HUMAN α9-INTEGRIN ANTIBODY

(75) Inventors: Kenji Uehara, Kikuchi (JP); Hirofumi Higuchi, Kikuchi (JP); Toshihiro Nakashima, Kikuchi (JP); Daisuke Ishikawa, Kikuchi (JP); Nobuchika Yamamoto, Tokyo (JP); Hirotada Fujita, Tokyo (JP); Fumihiko Sakai, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 260 days.

(21) Appl. No.: 12/812,341

(22) PCT Filed: Jan. 9, 2009

(86) PCT No.: PCT/JP2009/050187
§ 371 (c)(1),
(2), (4) Date: Nov. 16, 2010

(87) PCT Pub. No.: WO2009/088064
PCT Pub. Date: Jul. 16, 2009

(65) Prior Publication Data
US 2011/0059077 A1    Mar. 10, 2011

(30) Foreign Application Priority Data

Jan. 11, 2008  (JP) ................................. 2008-004975
Oct. 31, 2008  (JP) ................................. 2008-282496

(51) Int. Cl.
*A61K 39/395* (2006.01)

(52) U.S. Cl.
USPC .................. 424/133.1; 530/387.3; 530/387.7; 530/388.22; 530/388.8; 424/143.1; 424/155.1; 424/174.1; 536/23.5; 435/69.1; 435/320.1; 435/325

(58) Field of Classification Search
USPC ...................... 536/23.5; 435/69.1, 320.1, 325; 424/133.1, 143.1, 155.1, 174.1; 530/387.3, 387.7, 388.22, 388.8
See application file for complete search history.

(56) References Cited

U.S. PATENT DOCUMENTS

| 7,241,873 B2 * | 7/2007 | Uede et al. .................. 530/387.3 |
| 2005/0272668 A1 | 12/2005 | Yednock et al. |
| 2006/0002923 A1 | 1/2006 | Uede et al. |
| 2008/0152653 A1 | 6/2008 | Kurotaki et al. |
| 2009/0252734 A1 | 10/2009 | Kanayama et al. |

FOREIGN PATENT DOCUMENTS

| WO | WO 03/027151 A1 | 4/2003 |
| WO | WO 2006/026759 A2 | 3/2006 |
| WO | WO 2006/075784 A1 | 7/2006 |
| WO | WO 2008/007804 A1 | 1/2008 |

OTHER PUBLICATIONS

Rudikoff et al (Proc. Natl. Acad. Sci. USA. 1982; 79: 1979-1983).*
Kanayama et al. (J. Immunol. Jun. 15, 2009; 182 (12): 8015-25).*
Mariuzza et al. (Annu. Rev. Biophys. Biophys. Chem. 1987; 16: 139-159).*
Winkler et al. (J. Immunol. Oct. 15, 2000; 165 (8): 4505-4514).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Wang et al. (Am. J. Respir. Cell. Mol. Biol. Nov. 1996; 15 (5): 664-72).*
Hongwei Rao, et al., "$α_9β_1$: A Novel Osteoclast Integrin That Regulates Osteoclast Formation and Function", Journal of Bone and Mineral Research, vol. 21, No. 10, 2006. pp. 1657-1665.
Guangwu Xu, et al., "Role of Osteopontin in amplification and perpetuation of rheumatoid synovitis", The Journal of Clinical Investigation, vol. 115, No. 4, Apr. 2005, pp. 1060-1067.
Angela Wang, et al., "Differential Regulation of Airway Epithelial Integrins by Growth Factors", Am. J. Respir. Cell Mol. Biol., vol. 15, No. 5, 1996, pp. 664-672.
Martine Verhoeyen, et al., "Reshaping Human Antibodies: Grafting an Antilysozyme Activity", Science, vol. 239, 1988, pp. 1534-1536.
Cary Queen, et al., "A humanized antibody that binds to the interleukin 2 receptor", Proc. Natl. Acd. Sci., vol. 86, 1989, pp. 10029-10033.

(Continued)

*Primary Examiner* — Stephen Rawlings
(74) *Attorney, Agent, or Firm* — Oblon, Spivak, McClelland, Maier & Neustadt, L.L.P.

(57) ABSTRACT

The present invention provides a humanized anti-human α9 integrin antibody having improved activity and/or property as compared to a donor mouse anti-human α9 integrin antibody, namely, a humanized anti-human α9 integrin antibody containing a heavy-chain variable region consisting of the amino acid sequence shown by SEQ ID NO:11 and a light-chain variable region consisting of the amino acid sequence shown by SEQ ID NO:17, a humanized anti-human α9 integrin antibody containing a heavy-chain variable region consisting of the amino acid sequence shown by SEQ ID NO:13 and a light-chain variable region consisting of the amino acid sequence shown by SEQ ID NO:17, a humanized anti-human α9 integrin antibody containing a heavy-chain variable region consisting of the amino acid sequence shown by SEQ ID NO:15 and a light-chain variable region consisting of the amino acid sequence shown by SEQ ID NO:9, and a means for the prophylaxis or treatment of various diseases involving human α9 integrin in the pathogenesis, which uses the antibody.

14 Claims, 5 Drawing Sheets

(56) References Cited

OTHER PUBLICATIONS

Yasuyuki Yokosaki, et al., "The Integrin $\alpha_9\beta_1$ Binds to a Novel Recognition Sequence (SVVYGLR) in the Thrombin-cleaved Amino-terminal Fragment of Osteopontin", J. Biol. Chem., vol. 274, No. 51, 1999, pp. 36328-36334.

Victoria Pham, et al., "De novo proteomic sequencing of a monoclonal antibody raised against OX40 ligand", Analytical Biochemistry, 352(1), May 1, 2006, pp. 77-86.

Benny K. C. Lo, "Antibody Humanization by CDR Grafting", Methods in Molecular Biology, vol. 248, 2004, pp. 135-159.

Edward N. van den Brink, et al., "Two classes of germline genes both derived from the $Vh_H1$ family direct the formation of human antibodies that recognize distinct antigenic sites in the C2 domain of factor VIII", Blood, vol. 99, No. 8, Apr. 15, 2002, pp. 2828-2834 (plus cover page).

Jonathan P. L. Cox, et al., "A directory of human germ-line $V_\chi$ segments reveals a strong bias in their usage", Eur. J. Immunol., vol. 24, No. 4, Apr. 1994, pp. 827-836.

H.-Gustav Klobeck, et al., "Subgroup IV of human immunoglobulin κ light chains is encoded by a single germline gene", Nucleic Acids Research, vol. 13, No. 18, Sep. 25, 1985, pp. 6515-6529.

Charles J. Epstein, "Non-randomness of Amino-acid Changes in the Evolution of Homologous Proteins", Nature, vol. 215, Jul. 22, 1967, pp. 355-359.

Wei-Ping Yang, et al., "CDR Walking Mutagenesis for the Affinity Maturation of a Potent Human Ani-HIV-1 Antibody into the Picomolar Range", J. Mol. Biol., vol. 254, Dec. 1, 1995, pp. 392-403.

H. Wu, et al., "Stepwise in vitro affinity maturation of Vitaxin, an $\alpha_v\beta_3$-specific humanized mAb", Proc. Nat'l. Acad. Sci. USA, vol. 95, pp. 6037-6042, May 1998.

\* cited by examiner

FIG. 1

```
              FR1                    CDR1        FR2              CDR2
Y9A2VH   QVQLQQSGAELANPGASVKMSCKASGYTLT  TYWMH  WVKQRPGQGLEWIG  YINPSSGYTEYNQKFKD

FR3                     CDR3          FR4
         KATLTADKSSSTAYMQLTSLTSEDSAVYYCAI  YGDYGDFYFDY  WGQGTTLTVSS
```

FIG. 2

```
              FR1                    CDR1         FR2            CDR2
Y9A2VL   SIVMTQTPKFLLVSAGDRVTMTC  KASQSVNTDVA  WFQQKPGQSPKLLIY  FASNHYT

FR3                CDR3        FR4
         GVPDRFTGSGYGTDFTFTISTVQAEDLAIYFC  RQDYSSPFT  FGGGTKLEIKR
```

FIG. 3

```
                    #RY9A2VH-01
             10    ↓   20         30         40         50         60
5'-CAGCAAGCTTGCCGCCACCATGGAATGGAGCTGGATCTTTCTCTTCCTCCTGTCAGTAAC
                     M  E  W  S  W  I  F  L  F  L  L  S  V  T 70         80         90        100        110        120
TGCAGGTGTCCAATCCCAGGTGCAGCTGGTGC-3'
    3'-TTAGGGTCCACGTCGACCACGTCAGACCCCGACTCCACTTCTTCGGACC
  A  G  V  Q  S  Q  V  Q  L  V  Q  S  G  A  E  V  K  K  P  G
                                              #RY9A2VH-03
            130        140        150    ↓  160        170        180
                             5'-AGGCTTCTGGATACACCCTCACCACCTACTGGATGCA
CAGGAGGCACTTCTACAGGACGTTCCGAAGACCTATGTGGAGTGG-5'
  S  S  V  K  M  S  C  K  A  S  G  Y  T↑L  T  T  Y  W  M  H
                                              #RY9A2VH-07
            190        200        210        220        230        240
CTGGGTGAAACAGAGACCTGGACAAGGGCTTGAGTGGATTGGATACATTAATCCTAGCT-3'
                                3'-CCTAACCTATGTAATTAGGATCGAG
  W  V  K  Q  R  P  G  Q  G  L  E  W  I  G  Y  I  N  P  S  S
                                                  #RY9A2VH-05
            250        260        270        280        290    ↓  300
                                                      5'-GGACAAATC
ACCAATATGACTTATGTTAGTCTTCAAGTTCCTGTCTCAGTGCTAATGGCGCCTGTTTAG
  G  Y  T  E  Y  N  Q  K  F  K  D  R  V  T  I  T  A  D  K  S 310        320        330        340        350        360
CACGAGCACAGCCTACATGGAGCTGAGCAGCCTGAGATCTGAGGACACGGCCGTGTATTA
GTGCTCGTGTCG-5'
  T  S↑T  A  Y  M  E  L  S  S  L  R  S  E  D  T  A  V  Y  Y
#RY9A2VH-08
            370        380        390        400        410        420
CTGTGCGATTTATGGTGACTATGG-3'
3'-GACACGCTAAATACCACTGATACCCCTAAAGATGAAACTGATGACCCCGTTCCCTGGTG
  C  A  I  Y  G  D  Y  G  D  F  Y  F  D  Y  W  G  Q  G  T  T 430        440        450        460
CCAGTGGCAGAGGAGTCCACTCACCTAGGCGCT-5'
  V  T  V  S  S              ↑
                        #RY9A2VH-06
```

FIG. 4

```
            #RY9A2VL-01
        10    ↓   20         30         40         50         60
5'-CAGCAAGCTTGCCGCCACCATGAAGTTGCCTGTTAGGCTGTTGGTGCTGATGTTCTGGAT
                       M  K  L  P  V  R  L  L  V  L  M  F  W  I 70         80         90        100        110        120
TCCTGCTTCCAGCAGTGACATCCAGATGACCCA-3'
       3'-GTCACTGTAGGTCTACTGGGTCAGAGGTAGGAGGACAGACGTAGACA
    P  A  S  S  S  D  I  Q  M  T  Q  S  P  S  S  L  S  A  S  V
                                                 #RY9A2VL-03
        130        140        150        160   ↓  170        180
                                5'-AGGCCAGTCAGAGTGTGAATACTGATGTTGCTTG
TCCTCTGTCTCAGTGGTAGTGAACGTTCCGGTCAGTCTCACACTTAT-5'
    G  D  R  V  T  I  T  C  K  A  S  Q  S  V  N  T  D  V  A  W
                                      #RY9A2VL-02
        190        200        210        220        230        240
GTATCAGCAGAAACCAGGGAAAGCCCCTAAGCTCCTGATCTACTTTGCATCCAATCAC-3'
                                3'-GACTAGATGAAACGTAGGTTAGTGAT
    Y  Q  Q  K  P  G  K  A  P  K  L  L  I  Y  F  A  S  N  H  Y
                                                 #RY9A2VL-05
        250        260        270        280        290   ↓  300
                                            5'-CAGATTTTACTTTCACCAT
GTGACCCCAGGGTAGTTCCAAGTGACCTTGAGCTAGACCCTGTCTAAAATGAAAGTGGTA
    T  G  V  P  S  R  F  S  G  S  G  S  G  T  D  F  T  F  T  I
                                                 #RY9A2VL-04
        310        320        330        340        350        360
CAGCAGCCTGCAGCCTGAAGATATTGCAACATATTACTGTCGGCAGGATTACAGCTCTCC
GTCGT-5'                                     3'-AATGTCGAGAGG
    S  S  L  Q  P  E  D  I  A  T  Y  Y  C  R  Q  D  Y  S  S  P 370        380        390        400        410        420
GTTCACGTT-3'
CAAGTGCAAGCCGCCTCCGTGGTTCCACCTCTAGTTTGCACTGATCTTAAATTTGAAACG
    F  T  F  G  G  G  T  K  V  E  I  K  R 430        440
AAGGAGTCAACCTAGGCGCT-5'
          ↑
    #RY9A2VL-06
```

HUMANIZED ANTI-HUMAN α9-INTEGRIN
ANTIBODY

CROSS REFERENCE TO RELATED APPLICATION

This application is a 371 of PCT/JP09/050187, filed on Jan. 9, 2009, and claims priority to the following Japanese Patent Applications: JP 2008-004975, filed on Jan. 11, 2008; and JP 2008-282496, filed on Oct. 31, 2008.

TECHNICAL FIELD

The present invention relates to an improved humanized anti-human α9 integrin antibody. More particularly, it relates to an improved humanized Y9A2 antibody having an activity to bind to a human α9 integrin protein to inhibit α9 integrin-dependent cell adhesion, and improved activity and/or property as compared to mouse anti-human α9 integrin antibody Y9A2. The humanized antibody is expected to be a drug for the diagnosis, prevention or treatment of autoimmune diseases such as rheumatoid arthritis, immune diseases such as allergies and graft rejections, and other various diseases involved by α9 integrin in their pathogenesis.

BACKGROUND ART

Integrin, a cell surface glycoprotein, is an adhesion molecule that functions mainly as a receptor for cell adhesion to extracellular matrices (collagen, laminin and the like) and members of the immunoglobulin family (ICAM-1, VCAM-1 and the like), and mediates signal transduction from extracellular matrices. Thereby, cells receive signals from the extracellular matrices, and differentiation, proliferation, cell death and the like are induced. Integrin is a hetero-dimer consisting of the two subunits α chain and β chain; there are different α chains and β chains occurring in a wide variety of combinations, and there are 24 members of the integrin superfamily. Integrin-knockout mice are fatal or diseased irrespective of which subunit is lacked, suggesting that individual integrins are necessary for the maintenance of life. Therefore, integrin, which transmits information on ambient conditions to cells to stimulate their responses, are thought to function in all situations of biological phenomena, and to mediate a broad range of pathologic conditions.

As such, integrin is indispensable to the survival of organisms, and is thought to play roles even in diseased states; some cases have been reported in which their inhibition helps improve pathologic conditions. For example, an inhibitor of platelet-specific integrin αIIbβ3 has been approved as a therapeutic drug for PCTA restenosis known as abciximab (trade name: ReoPro; Eli Lilly). Natalizumab (trade name: Antegren; ELAN Company), an α4β1 (VLA4) inhibitor, has been approved as a therapeutic drug for multiple sclerosis. The αvβ3 inhibitor Vitaxin (MEDIMMUNE Company) is under development in clinical studies for its neovascularization inhibitory action, osteoclast activation inhibitory action and the like.

Integrin α9β1 is expressed in macrophages, NKT cells, dendritic cells, and neutrophils, and reportedly plays important roles in the infiltration and adhesion of these inflammatory cells, bone resorption and the like. Recently, it has been reported that integrin α9β1 is involved in osteoclast formation, and its involvement in bone destruction has been suggested (Non-patent Document 1). Known ligands thereof include truncated osteopontin (N-terminal OPN), VCAM-1, Tenascin-C and the like. Clinically, significantly elevated levels of integrin and have been observed in the synovial tissues of patients with rheumatoid arthritis (Non-patent Document 2).

Therefore, a monoclonal antibody that binds specifically to α9 integrin protein to act to inhibit α9 integrin-dependent cell adhesion, if developed, would be useful in the diagnosis, prevention or treatment of various diseases involved by α9 integrin in their pathogenesis.

Antibodies that have been reported to exhibit function inhibitory action on human α9 integrin are the mouse monoclonal antibody Y9A2 (Non-patent Document 3), and 1K11, 24I11, 21C5 and 25B6 (Patent Document 1) and 28S1 (Patent Document 2). In vitro experimental results have shown that these antibodies are capable of suppressing human α9 integrin-dependent cell adhesion. Among those, since Y9A2 inhibits cell adhesion to both osteopontin and Tenascin-C, it is considered most promising as a candidate for an antibody drug against α9 integrin.

It should be noted, however, that Y9A2 is a mouse-derived antibody prepared by immunizing a mouse with an antigen, and therefore, direct administration thereof to human is practically impossible from the aspects of safety (induction of antigenicity) and effectiveness (shortened half-life). Therefore, a modification to convert the antibody to a molecule having an amino acid sequence of human antibody while maintaining the activity of Y9A2, i.e., humanization, needs to be performed.

At present, as a production method of humanized antibody, a method based on the method including grafting of amino acid of complementarity determining region (hereinafter sometimes to be indicated as CDR) as designed by Winter et al. (non-patent document 4) is most general. It is also well known here that simultaneous grafting of not only CDR but also non-CDR amino acid involved in the structural maintenance of CDR or binding with an antigen, i.e., a framework region (hereinafter sometimes to be indicated as FR), from a foreign antibody to be the donor of CDR amino acid to a human antibody to be the acceptor of CDR is important for the reproduction of the inherent activity of the donor antibody (non-patent documents 4 and 5).

However, production of a humanized antibody based on CDR grafting includes several problems. Firstly, the most general problem is that even an appropriate selection of FR amino acid necessary for reproduction of the activity of a donor antibody cannot eliminate the difficulty of obtaining a humanized antibody having affinity to an antigen and biological activity exceeding those of the donor antibody.

In recent years, a large number of chimeric antibody, humanized antibody and human antibody has been placed in the market as monoclonal pharmaceutical products. The effective dose of any of them is extremely high and is several mg per 1 kg body weight. Therefore, antibody pharmaceuticals are inevitably expensive, which in turn increases economical burden on the patients and medical costs. The major factors defining the effective dose of an antibody drug include affinity of the antibody to an antigen and the amount of the antigen present in the body. From such aspects, particularly, an improvement in the affinity of an antibody to an antigen leads to a reduction in the dose, and is an extremely useful improvement also resulting in the reduction of economical burden on the patients and medical costs.

To realize an improved affinity of an antibody to an antigen, a method including introduction of amino acid substitution into a variable region of the antibody is often adopted. However, when antibody and antigen are different, the sequence and steric structure of CDR amino acid, as well as the position of amino acid involved in antigen-antibody interactions also vary. Therefore, it is practically impossible to define the position of FR amino acid to be grafted together with CDR as being applicable to any antibody.

Another problem is that, while the whole CDR amino acid of a donor mouse antibody is generally grafted to a template human antibody in the preparation of a humanized antibody based on CDR grafting, an amino acid sequence of CDR derived from a mouse antibody, which is important for binding with an antigen, sometimes shows antigenicity against human, often causing generation of an anti-idiotype antibody.

That is, for the production of a humanized antibody, selection of an appropriate acceptor antibody and selection of CDR amino acid and FR amino acid to be substituted are indispensable for imparting an activity higher than that of a donor antibody while avoiding generation of antigenicity in human and lowered stability of the antibody. These require considerable ingenuity and trial and error.

patent document 1: WO 2006/075784
patent document 2: WO 2008/007804
non-patent document 1: Journal of Bone and Mineral Research, 2006, 21: 1657-1665
non-patent document 2: The Journal of Clinical Investigation, 2005, 115: 1060-1067
non-patent document 3: Am. J. Respir. Cell Mol. Biol., 1996, 15: 664-672
non-patent document 4: Science, 239, 1534-1536 (1988)
non-patent document 5: Proc. Natl. Acad. Sci. USA, 86, 10029-10033 (1989)

DISCLOSURE OF THE INVENTION

Problems to be Solved by the Invention

An object of the present invention is to solve the above-mentioned various problems relating to humanized antibodies, and provide a humanized anti-human α9 integrin antibody having improved activity and/or property as compared to a donor mouse anti-human α9 integrin antibody (Y9A2).

Means of Solving the Problems

Accordingly, the present invention comprises the inventions of the following (1)-(15) as medically or industrially useful substances and methods.

(1) A humanized anti-human α9 integrin antibody comprising a heavy chain variable region and a light chain variable region selected from the following:
(a) a heavy-chain variable region consisting of the amino acid sequence shown by SEQ ID NO:11 and a light-chain variable region consisting of the amino acid sequence shown by SEQ ID NO:17
(b) a heavy-chain variable region consisting of the amino acid sequence shown by SEQ ID NO:13 and a light-chain variable region consisting of the amino acid sequence shown by SEQ ID NO:17, and
(c) a heavy-chain variable region consisting of the amino acid sequence shown by SEQ ID NO:15 and a light-chain variable region consisting of the amino acid sequence shown by SEQ ID NO:9.
(2) The humanized anti-human α9 integrin antibody described in (1) above, wherein the heavy-chain constant region of the antibody is human Igγ1.
(3) The humanized anti-human α9 integrin antibody described in (1) above, wherein the light-chain constant region of the antibody is human Igκ.
(4) The humanized anti-human α9 integrin antibody described in (1) above, wherein the heavy-chain constant region of the antibody is human Igγ1 and the light-chain constant region of the antibody is human Igκ.
(5) The humanized anti-human α9 integrin antibody described in (1) above, wherein the heavy chain consists of the amino acid sequence shown by SEQ ID NO:19 and the light-chain consists of the amino acid sequence shown by SEQ ID NO:25.
(6) The humanized anti-human α9 integrin antibody described in (1) above, wherein the heavy chain consists of the amino acid sequence shown by SEQ ID NO:21 and the light-chain consists of the amino acid sequence shown by SEQ ID NO:25.
(7) The humanized anti-human α9 integrin antibody described in (1) above, wherein the heavy chain consists of the amino acid sequence shown by SEQ ID NO:23 and the light chain consists of the amino acid sequence shown by SEQ ID NO:27.
(8) A polynucleotide comprising a sequence encoding the heavy-chain variable region of the humanized anti-human α9 integrin antibody described in (1) above.
(9) A polynucleotide comprising a sequence encoding the light-chain variable region of the humanized anti-human α9 integrin antibody described in (1) above.
(10) An expression vector comprising the polynucleotide described in (8) and/or the polynucleotide described in (9) above.
(11) A host cell incorporating the expression vector described in (10) above.
(12) A method of producing a humanized anti-human α9 integrin antibody, comprising a step of culturing the host cell described in (11) above to allow expression of the humanized anti-human α9 integrin antibody.
(13) A therapeutic drug for rheumatoid arthritis, comprising the humanized anti-human α9 integrin antibody described in any of (1) to (7) above.
(14) A method of preventing or treating rheumatoid arthritis, comprising a step of administering a therapeutically effective amount of the humanized anti-human α9 integrin antibody described in any of (1) to (7) above.
(15) A use of the humanized anti-human α9 integrin antibody described in any of (1) to (7) above in the manufacture of a pharmaceutical for preventing or treating rheumatoid arthritis.

Effect of the Invention

According to the present invention, a humanized anti-human α9 integrin antibody having an improved activity and/or property as compared to a donor mouse anti-human α9 integrin antibody is provided. The humanized anti-human α9 integrin antibody of the present invention has a strong anti-inflammatory action and a strong bone destruction suppressive action by blocking interactions between human α9 integrin and plural ligands thereof, and is useful for the prophylaxis or treatment of various diseases involving human α9 integrin in the pathogenesis. Moreover, the humanized anti-human α9 integrin antibody of the present invention provides superior improvements in clinical applications such as reduction of dose, extension of administration interval, improvement of administration method (e.g., subcutaneous injection) and the like, and greatly contributes to the therapeutic effectiveness and improvement of patients compliance.

BRIEF DESCRIPTION OF THE DRAWINGS

FIG. 1 shows the amino acid sequence of the VH region of a mouse Y9A2 antibody (SEQ ID NO: 1).

FIG. 2 shows the amino acid sequence of the VL region of a mouse Y9A2 antibody (SEQ ID NO: 3).

FIG. 3 shows the constitution of oligoDNA (SEQ ID NOS: 29, 33, 30, 34, 31 and 32, respectively, in order of appearance) for producing a gene encoding RY9A2VHv5, which is one example of VH of a humanized Y9A2 antibody (SEQ ID NO: 45).

FIG. 4 shows the constitution of oligoDNA (SEQ ID NOS: 37-42, respectively, in order of appearance) for producing a gene encoding RY9A2VLv01, which is one example of VL of a humanized Y9A2 antibody (SEQ ID NO: 46).

BEST MODE FOR CARRYING OUT THE INVENTION

Figure 5:
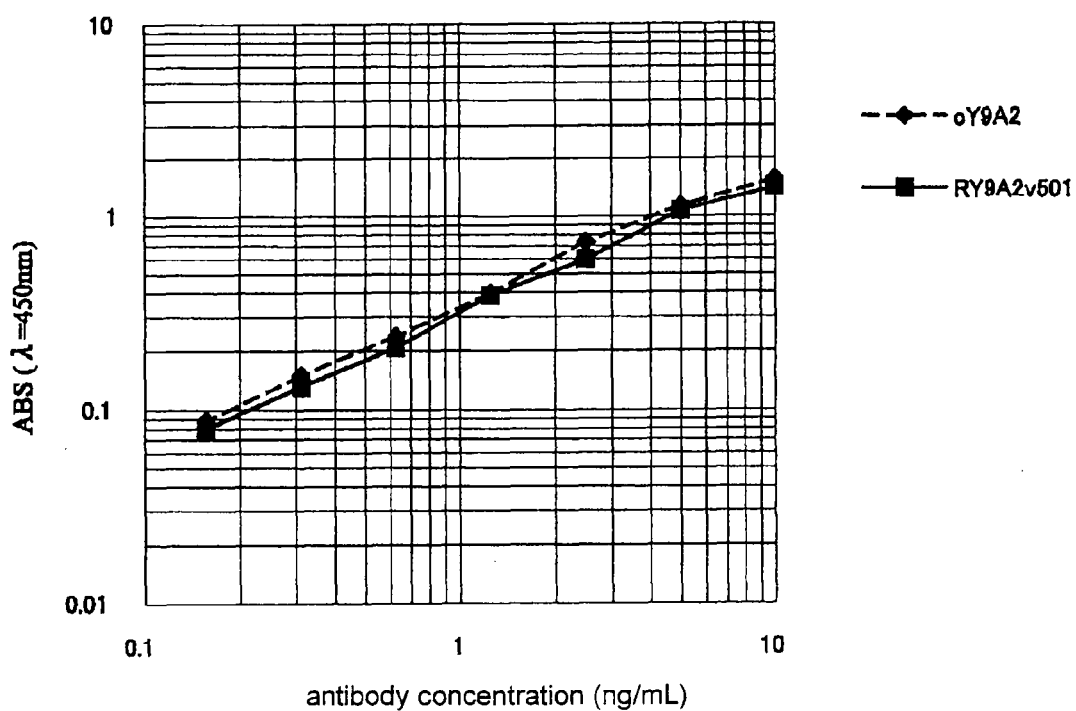
FIG. 5 shows the results of Cell ELISA of a chimeric Y9A2 antibody and an RY9A2v501 antibody.

The present invention is described in detail in the following.

The present inventors have demonstrated considerable ingenuity and consideration for the production of a humanized antibody of mouse anti-human α9 integrin antibody Y9A2, and succeeded in producing three kinds of humanized anti-human α9 integrin antibodies (hereinafter to be also referred to as humanized Y9A2 antibody or RY9A2) having significantly improved activities and/or properties as compared to Y9A2.

To be specific, the present inventors first grafted CDR amino acid sequence and several FR amino acids of a heavy chain variable region (hereinafter to be also referred to as VH) and a light chain variable region (hereinafter to be also referred to as VL) of mouse anti-human α9 integrin antibody Y9A2 (hereinafter to be also referred to as mouse Y9A2 antibody) into a template human antibody to prepare two kinds of humanized anti-human α9 integrin antibodies RY9A2v501 and RY9A2v801 each having an activity equivalent to that of a mouse Y9A2 antibody. CDR was determined according to the classification by Kabat et al. (Sequences of Proteins of Immunological Interest 4th ed., Public Health Service, NIH, Washington D.C., 1987). The amino acid sequences of VHs of RY9A2v501 and RY9A2v801 are SEQ ID NO: 5 and SEQ ID NO: 7, respectively. Here, VH of RY9A2v801 is VH of RY9A2v501 wherein 4 amino acid residues from FR amino acid residues derived from mouse Y9A2 antibody are substituted by the corresponding template human antibody amino acids. The amino acid sequence of VLs of the both humanized antibodies is shown by SEQ ID NO: 9 and is common to the both antibodies.

Next, with the aim of producing a humanized antibody having higher affinity to human α9 integrin than that of the original mouse Y9A2 antibody, while avoiding the risk of production of antigenicity of a humanized antibody and lowered preservation stability of the antibody, the present inventors considered substitution of amino acid sequences in the CDRs of VH and VL of the above-mentioned two kinds of humanized antibodies. As a result, the following 3 kinds of humanized anti-human α9 integrin antibodies were confirmed to have significantly improved activities and/or properties as compared to those of the original mouse Y9A2 antibody.

1) A humanized anti-human α9 integrin antibody comprising a heavy-chain variable region consisting of the amino acid sequence shown by SEQ ID NO:11 and a light-chain variable region consisting of the amino acid sequence shown by SEQ ID NO:17.

2) A humanized anti-human α9 integrin antibody comprising a heavy-chain variable region consisting of the amino acid sequence shown by SEQ ID NO:13 and a light-chain variable region consisting of the amino acid sequence shown by SEQ ID NO:17.

3) A humanized anti-human α9 integrin antibody comprising a heavy-chain variable region consisting of the amino acid sequence shown by SEQ ID NO:15 and a light-chain variable region consisting of the amino acid sequence shown by SEQ ID NO:9.

The humanized anti-human α9 integrin antibody of the present invention can easily be prepared by those skilled in the art on the basis of the sequence information on the heavy-chain variable region and light-chain variable region thereof disclosed herein, using a method commonly known in the art. Specifically, a heavy-chain variable region gene segment having a base sequence that encodes the heavy-chain variable region amino acid of the humanized antibody of the present invention, and a light-chain variable region gene segment having a base sequence that encodes the light-chain variable region amino acid of the humanized antibody of the present invention are prepared. Then, the variable region genes are joined to a constant region gene in an appropriate class of human antibody to prepare a humanized antibody gene. Next, this humanized antibody gene is joined to an appropriate expression vector, and introduced into a cultured cell. Finally, this cultured cell is cultured, whereby a humanized antibody can be obtained from the culture supernatant.

Each of the above-described variable region gene segments that encode the heavy-chain and light-chain variable region amino acids of the humanized antibody of the present invention can be synthesized, for example, based on the base sequences of the heavy chain and light chain variable regions or base sequences designed based on the amino acid sequences of the heavy chain and light chain variable regions and by a gene synthesis method known in the art. As such gene synthesis method, various methods known to those of ordinary skill in the art such as the antibody gene synthesis method described in WO90/07861 and the like can be used. In addition, once a variable region gene segment of the antibody of the present invention is acquired, other antibodies of the present invention can also be acquired by introducing a mutation into a given site of the gene segment. As such mutation introduction method, various methods obvious to those skilled in the art, such as site-directed mutagenesis (Current Protocols in Molecular Biology edit. Ausubel et al. (1987) Publish. John Wiley & Sons Section 8.1-8.5) can be used.

Next, the above-described variable region gene segments and the constant region gene of the human antibody are joined to prepare a humanized antibody gene. While any subclass of constant region (e.g., γ1, γ2, γ and γ4 as heavy chains, λ and κ chain constant regions as light chains) can be chosen as the constant region of the human antibody used, human Igγ1 as the heavy-chain constant region, and human Igκ as the light-chain constant region, can be preferably used.

Subsequent to the preparation of this humanized antibody gene, introduction of the humanized antibody gene to an expression vector, introduction of the expression vector to cultured cells, cultivation of the cultured cells, purification of the antibody and the like can be performed by using various methods commonly known in the art, or with reference to the methods of preparing a humanized anti-human osteopontin antibody, described in WO2007/139164 or WO2003/027151.

As the expression vector to be joined to the humanized antibody gene thus obtained, the expression vectors described in International Patent Publication Official Gazette WO94/20632, such as AG-γ1 and AG-κ, can be used, but the expression vector is not subject to limitation, as long as it is capable of expressing the humanized antibody gene. It is preferable to utilize an expression vector already having a human Ig constant region gene such as AG-γ1 or AG-κ, because it would become an expression vector having the humanized antibody gene simply when the humanized antibody variable region gene is inserted thereto. In an expression vector, a leader sequence may be used to promote extracellular secretion and expression of an antibody. As such leader sequence, a leader sequence derived from Y9A2 or a leader sequence derived from other antibody (e.g., humanized anti-osteopontin antibody described in WO2007/139164) can be used.

The above-described expression vector is introduced into cultured cells by, for example, using a FreeStyle 293 Expression system (Invitrogen), a calcium phosphate method and the like.

As examples of the cultured cells to which the expression vector is introduced, cultured cells such as 293 cells, CHO-DG44 cells can be used, and they may be cultured by a conventional method.

After the above-described cultivation, the antibody accumulated in the culture supernatant can be purified by various kinds of column chromatographies, for example, chromatographies using a Protein A column.

As a method for measuring the binding activity of the obtained humanized antibody to human α9 integrin, ELISA, FACS and the like can be used. When ELISA is used, for example, cells (e.g., SW480 cell) expressing α9 integrin are immobilized on an ELISA plate, a humanized antibody is added thereto to cause reaction, and a secondary antibody such as a human IgG antibody labeled with an enzyme such as horseradish peroxidase (HRP) is added thereto to cause reaction. The cells are washed, a color development substrate (e.g., TMB when HRP labeling) is added thereto, and the absorbance is measured.

As a method for evaluating whether the obtained humanized antibody has a function inhibitory activity against human α9 integrin, it can be confirmed by an inhibition test (described in J. Biol. Chem., 274:36328-36334, 1999) of human α9 integrin molecule-dependent cell adhesion to human osteopontin molecule. That is, RAA variant (RGD sequence is altered to RAA to suppress reaction with other integrin; hereinafter sometimes to be indicated as nOPN-RAA) of N-terminal OPN(N terminal fragment after cleavage of osteopontin by thrombin; hereinafter sometimes to be indicated as nOPN), which is one of the α9 ligands, is immobilized on a plate and subjected to blocking. After addition of various humanized antibodies, α9 expression cells are added and incubated at 37° C. for 1 hr. The cells are fixed and stained with crystal violet and methanol, and washed. The dye in the adhered cells is extracted with Triton X-100, and the absorbance at wavelength 595 nm is measured.

Furthermore, as a method for detailedly evaluating whether the obtained humanized antibody has a function inhibitory activity against human α9 integrin, a method based on the cell migration inhibition test described in Molecular Biology of the cell, 12: 3214-3225, 2001, can be mentioned. That is, nOPN-RAA is immobilized on the upper layer of a transwell and set on a plate, and then F15 medium containing 10% FCS is added to the lower layer. α9 expression cell and humanized antibody are simultaneously added to the upper layer and incubated at 37° C. for 16 hr. Thereafter, the cells migrated into the lower layer of the transwell are quantified by, for example, QCM Chemotaxis Cell Migration 24-well Assay kit (Millipore).

The 3 kinds of humanized anti-human α9 integrin antibodies of the present invention can easily be acquired by synthesizing a DNA that encodes the VH amino acid sequence shown by SEQ ID NO:11, 13 or 15 and a DNA that encodes the VL amino acid sequence shown by SEQ ID NO:17 or 9 using a method commonly known in the art, joining them to an appropriate class of human antibody constant region gene, preferably the human Igγ1 constant region gene for the heavy chain and the human Igκ constant region gene for the light chain, to construct a humanized antibody gene, introducing the humanized antibody gene to an expression vector using various methods commonly known in the art or the method described in WO02/081522 or WO03/027151 and the like, introducing the expression vector to cultured cells, culturing the cultured cells, and purifying the antibody from the culture obtained. Preferably, DNAs encoding the VH amino acid sequences shown by SEQ ID NO: 11, 13 and 15 contain base sequences shown by SEQ ID NO: 12, 14 and 16, respectively. Preferably, DNAs encoding the VL amino acid sequences shown by SEQ ID NO: 17 and 9 contain base sequences shown by SEQ ID NO: 18 and 10, respectively.

The preferable humanized antibody heavy-chain of the present invention, which is obtained by joining the heavy-chain variable region shown by SEQ ID NO:11 and the human Igγ1 constant region, is a heavy chain consisting of the amino acid sequence shown by SEQ ID NO:19. The preferable humanized antibody light-chain of the present invention, which is obtained by joining the light-chain variable region shown by SEQ ID NO:17 and the human Igκ constant region, is a light chain consisting of the amino acid sequence shown by SEQ ID NO:25. Preferably, a DNA encoding the humanized antibody heavy chain consisting of the amino acid sequence shown by SEQ ID NO:19 contains the base sequence shown by SEQ ID NO:20. Preferably, a DNA encoding the humanized antibody light chain consisting of the amino acid sequence shown by SEQ ID NO:25 contains the base sequence shown by SEQ ID NO:26. As the humanized anti-α9 integrin antibody of the present invention containing a heavy chain consisting of the amino acid sequence shown by SEQ ID NO:19, and a light chain consisting of the amino acid sequence shown by SEQ ID NO:25, an RY9A2v12(M34L)012 antibody shown in the Examples described below can be mentioned.

The preferable humanized antibody heavy-chain of the present invention, which is obtained by joining the heavy-chain variable region shown by SEQ ID NO:13 and the human Igγ1 constant region, is a heavy chain consisting of the amino acid sequence shown by SEQ ID NO:21. The preferable humanized antibody light-chain of the present invention, which is obtained by joining the light-chain variable region shown by SEQ ID NO:17 and the human Igκ constant region, is a light chain consisting of the amino acid sequence shown by SEQ ID NO:25. Preferably, a DNA encoding the humanized antibody heavy chain consisting of the amino acid sequence shown by SEQ ID NO:21 contains the base sequence shown by SEQ ID NO:22. Preferably, a DNA encoding the humanized antibody light chain consisting of the amino acid sequence shown by SEQ ID NO:25 contains the base sequence shown by SEQ ID NO:26. As the humanized anti-α9 integrin antibody of the present invention containing a heavy chain consisting of the amino acid sequence shown by SEQ ID NO:21, and a light chain consisting of the amino acid sequence shown by SEQ ID NO:25, an RY9A2v11(M34L)012 antibody shown in the Examples described below can be mentioned.

The preferable humanized antibody heavy-chain of the present invention, which is obtained by joining the heavy-chain variable region shown by SEQ ID NO:15 and the human Igγ1 constant region is a heavy chain consisting of the amino acid sequence shown by SEQ ID NO:23. The preferable humanized antibody light-chain of the present invention, which is obtained by joining the light-chain variable region shown by SEQ ID NO:9 and the human Igκ constant region is a light chain consisting of the amino acid sequence shown by SEQ ID NO:27. Preferably, a DNA encoding the humanized antibody heavy chain consisting of the amino acid sequence shown by SEQ ID NO:23 contains the base sequence shown by SEQ ID NO:24. Preferably, a DNA encoding the humanized antibody light chain consisting of the amino acid sequence shown by SEQ ID NO:27 contains the base sequence shown by SEQ ID NO:28. As the humanized anti-α9 integrin antibody of the present invention containing a heavy chain consisting of the amino acid sequence shown by SEQ ID NO:23, and a light chain consisting of the amino acid sequence shown by SEQ ID NO:27, an RY9A2v05(IAW)01 antibody shown in the Examples described below can be mentioned.

The humanized anti-human α9 integrin antibody of the present invention thus obtained after being further purified as required can be prepared as a pharmaceutical preparation according to a conventional method, and used for the treatment of autoimmune diseases such as rheumatoid arthritis and the like, immune diseases such as allergy, transplant rejection and the like, and diseases wherein α9 integrin is involved in the pathogenesis such as osteoporosis, chronic obstructive pulmonary disease, cancer and the like.

The humanized anti-human α9 integrin antibody of the present invention can be used preferably as a therapeutic agent for rheumatoid arthritis. As examples of dosage forms for these therapeutic agents, a parenteral preparation such as an injection or drip infusion can be prepared, and is preferably administered by intravenous administration, subcutaneous administration and the like. In preparing a pharmaceutical preparation, carriers and additives that match these dosage forms can be used within a pharmaceutically acceptable range.

The amount of humanized anti-human α9 integrin antibody of the present invention added in the above-described preparation making varies depending on the patient symptom severity and age, the dosage form of the preparation used or the binding titer of the antibody and the like; for example, about 0.1 mg/kg to 100 mg/kg may be used.

The present invention also provides polynucleotide encoding the humanized anti-human α9 integrin antibody of the present invention or heavy chain and/or light chain variable regions thereof, and an expression vector containing same. The expression vector of the present invention is not subject to limitation, as long as it is capable of expressing a gene that encodes the humanized antibody of the present invention or a heavy-chain or light-chain variable region thereof in various host cells of prokaryotic cells and/or eukaryotic cells, and producing these polypeptides. For example, plasmid vectors, viral vectors (e.g., adenovirus, retrovirus) and the like can be mentioned.

The expression vector of the present invention can comprise a gene that encodes the humanized anti-human α9 integrin antibody of the present invention or a heavy-chain and/or light-chain variable region thereof, and a promoter functionally joined to the gene. As the promoter for expressing the gene that encodes the humanized antibody of the present invention or a heavy-chain and/or light chain variable region thereof in a bacterium, when the host is a bacterium of the genus *Escherichia*, for example, the Trp promoter, lac promoter, recA promoter, λPL promoter, lpp promoter, tac promoter and the like can be mentioned. As the promoter for expressing the gene that encodes the humanized antibody or a heavy-chain and/or light-chain variable region thereof in yeast, for example, the PH05 promoter, PGK promoter, GAP promoter, and ADH promoter can be mentioned; when the host is a bacterium of the genus *Bacillus*, the SL01 promoter, SP02 promoter, penP promoter and the like can be mentioned. When the host is a eukaryotic cell such as a mammalian cell, β actin promoter, CAG promoter (Niwa H. et al., Gene, 108, 193-200, 1991), the SV40-derived promoter, retrovirus promoter, heat shock promoter and the like can be mentioned.

When a bacterium, particularly *Escherichia coli*, is used m as the host cell, the expression vector of the present invention can further comprise an initiation codon, a stop codon, a terminator region and a replicable unit. When a yeast, animal cell or insect cell is used as the host, the expression vector of the present invention can comprise an initiation codon and a stop codon. In this case, an enhancer sequence, noncoding regions on the 5' side and 3' side of a gene that encodes the humanized antibody of the present invention or a heavy-chain and/or light-chain variable region thereof, a splicing junction, a polyadenylation site, or a replicable unit and the like may be contained. In addition, a selection marker (e.g., tetracycline resistance gene, ampicillin resistance gene, kanamycin resistance gene, neomycin resistance gene, dihydrofolate reductase gene) conventionally used according to the object may also be contained.

The present invention also provides a transformant incorporating a gene that encodes the humanized antibody of the present invention or a heavy-chain and/or light-chain variable region thereof. Such a transformant can be prepared by, for example, transforming a host cell with the expression vector of the present invention. The host cell used to prepare a transformant is not subject to limitation, as long as it matches the aforementioned expression vector, and is transformable; various cells such as natural cells or artificially established lines of cells in common use in the technical field of the present invention (e.g., bacteria (bacteria of the genus *Escherichia*, bacteria of the genus *Bacillus*), yeasts (the genus *Saccharomyces*, the genus *Pichia* and the like), animal cells or insect cells (e.g., Sf9) and the like) can be mentioned as examples. The transformation can be performed by a method known per se.

The present invention also provides a production method of the humanized anti-human α9 integrin antibody of the present invention comprising expressing a gene encoding the humanized antibody or heavy chain and/or light chain variable regions of the present invention in a host cell, namely, using such a transformant. Preferably, the host cell used for the method incorporates the expression vector of the present invention, and the expression vector may separately or simultaneously contain polynucleotides encoding the heavy chain and light chain variable regions of the humanized anti-human α9 integrin antibody.

In producing the humanized anti-human α9 integrin antibody of the present invention, the transformant can be cultured in nutrient medium. The nutrient medium preferably contains a carbon source and an inorganic nitrogen source or organic nitrogen source required for the growth of the transformant. As examples of the carbon source, glucose, dextran, soluble starch, sucrose and the like can be mentioned; as examples of the inorganic nitrogen source or organic nitrogen source, ammonium salts, nitrates, amino acids, corn steep liquor, peptone, casein, meat extract, soybean cake, potato extract and the like can be mentioned. If desired, other nutrients (e.g., inorganic salts (e.g., calcium chloride, sodium dihydrogen phosphate, magnesium chloride), vitamins, antibiotics (e.g., tetracycline, neomycin, ampicillin, kanamycin and the like) and the like) may be contained.

Cultivation of the transformant can be performed by a method known per se. Cultivation conditions, for example, temperature, pH of the medium, and cultivation time are selected as appropriate. For example, when the host is an animal cell, an MEM medium (Science, Vol. 122, p. 501, 1952), DMEM medium (Virology, Vol. 8, p. 396, 1959), RPMI1640 medium (J. Am. Med. Assoc., Vol. 199, p. 519, 1967), 199 medium (Proc. Soc. Exp. Biol. Med., Vol. 73, p. 1, 1950) containing about 5 to 20% fetal bovine serum and the like can be used as the medium. The pH of the medium is preferably about 6 to 8, cultivation is normally performed at about 30 to 40° C. for about 15 to 72 hours, and the culture may be aerated or agitated as necessary. When the host is an insect cell, for example, Grace's medium comprising fetal bovine serum (Proc. Natl. Acad. Sci. USA, Vol. 82, p. 8404, 1985) and the like can be mentioned, and the pH thereof is preferably about 5 to 8. Cultivation is normally performed at about 20 to 40° C. for 15 to 100 hours, and the culture may be aerated or agitated as necessary. When the host is a bacterium, an actinomyces, yeast, or a filamentous fungus, for example, a liquid medium comprising the above-described nutrient sources is appropriate. A medium having a pH of 5 to 8 is preferable. When the host is $E.$ $coli$, LB medium, M9 medium (Miller et al., Exp. Mol. Genet, Cold Spring Harbor Laboratory, p. 431, 1972) and the like can be mentioned as preferable media. In this case, cultivation can be normally performed at 14 to 43° C. for about 3 to 24 hours, while aerating or agitating the culture as necessary. When the host is a bacterium of the genus $Bacillus$, cultivation can be normally performed at 30 to 40° C. for about 16 to 96 hours, while aerating or agitating the culture as necessary. When the host is yeast, Burkholder's minimal medium (Bostian, Proc. Natl. Acad. Sci. USA, Vol. 77, p. 4505, 1980) can be mentioned as examples of the medium, and the pH is desirably 5 to 8. Cultivation is normally performed at about 20 to 35° C. for about 14 to 144 hours, and the culture may be aerated or agitated as necessary.

The humanized anti-human α9 integrin antibody of the present invention can be recovered, preferably isolated and purified, from a cultured transformant as described above. As examples of the method of isolation and purification, methods based on differences in solubility, such as salting-out and solvent precipitation; methods based on differences in molecular weight, such as dialysis, ultrafiltration, gel filtration, and sodium dodecyl sulfate-polyacrylamide gel electrophoresis; methods based on differences in electric charge, such as ion exchange chromatography and hydroxyl apatite chromatography; methods based on specific affinity, such as affinity chromatography; methods based on differences in hydrophobicity, such as reverse phase high performance liquid chromatography; methods based on differences in isoelectric point, such as isoelectric focusing electrophoresis; and the like can be mentioned.

The present invention is explained in detail in the following by referring to Examples, which are not to be construed as limitative.

EXAMPLES

As for the part where commercially available kits or reagents were used, unless otherwise specified, the experiments were performed according to the attached protocol.

Example 1

Determination of Mouse Y9A2 Antibody Variable Region Sequence and Production of Chimeric Y9A2 Antibody The heavy chain variable region (VH) and light chain variable region (VL) genes of mouse Y9A2 antibody were determined, and the VH gene was ligated to human Igγ1 gene and the VL gene was ligated to human Igκ gene to give a mouse-human chimeric antibody (hereinafter to be also referred to as chimeric Y9A2 antibody). The procedures are as follows.

First, RNA was extracted from mouse Y9A2 antibody producing hybridoma, which was supplied by University of California at San Francisco (UCSF), with a TRIzol reagent (Invitrogen). Using the RNA as a template, cDNA was synthesized by using Random Primer and SuperScript III Reverse Transcriptase (both Invitrogen). Then, using this cDNA as a template, and a primer to a leader region and a primer to the J region designed by reference to the classification of sequences of V region and J region by Kabat et al. (Sequences of Proteins of Immunological Interest 4th ed., Public Health Service, NIH, Washington D.C., 1987), a VH gene segment was amplified with Ex Taq DNA polymerase (TAKARA BIO INC.). The primer for the above-mentioned leader region and the primer for the J region used here are added with a HindIII recognition sequence and a BamHI recognition sequence, respectively. As for VL, a VL gene segment was obtained in the same manner as with VH by using a primer conforming to the leader sequence and a primer conforming to the J region.

The thus-obtained VH and VL gene segments were digested with HindIII and BamHI (both TAKARA BIO INC.), and ligated to AG-γ1 and AG-κ (WO94/20632), respectively, which are expression vectors. AG-γ1 has a β actin promoter, a gene of human immunoglobulin constant region γ1 chain, and a neomycin resistance gene (neo) as a selection marker, and becomes a plasmid expressing a heavy chain of chimeric Y9A2 antibody by inserting a mouse Y9A2 antibody VH gene between a HindIII recognition sequence and a BamHI recognition sequence located upstream of γ1 gene. AG-κ has a β actin promoter, a gene of human immunoglobulin constant region κ chain, and a dihydrofolate reductase (dhfr) gene as a selection marker, and similarly becomes a plasmid expressing a light chain of chimeric Y9A2 antibody by inserting a mouse Y9A2 antibody VL gene between a HindIII recognition sequence and a BamHI recognition sequence located upstream of κ gene.

These expression plasmids were introduced into $Escherichia$ $coli$ according to a conventional method to give a transformed clone, from which plasmid DNA was prepared using a QIAprep Spin Miniprep Kit (QIAGEN). Using the obtained plasmid DNA as a template, and GenomeLab DTCS-Quick Start Kit and a CEQ2000 automatic sequencer (both BECKMAN COULTER), cloned VH and VL base sequences were analyzed. The base sequences of VH and VL are shown in SEQ ID NO: 2 and SEQ ID NO: 4, respectively. The amino acid sequences of VH and VL, which were determined based on the obtained sequences, are shown in FIG. 1 and FIG. 2, respectively. In addition, they are shown in SEQ ID NO: 1 and SEQ ID NO: 3, respectively.

The above-mentioned $Escherichia$ $coli$ clone was cultured in large amounts, and the heavy chain expression plasmid and light chain expression plasmid of chimeric Y9A2 antibody were purified using an EndoFree Plasmid Maxi Kit (QIAGEN). They were mixed, and introduced into the cell using FreeStyle 293 Expression System (Invitrogen), whereby chimeric Y9A2 antibody was transiently expressed. The concentration of the chimeric Y9A2 antibody contained in the obtained culture supernatant was measured by sandwich ELISA using a goat-derived anti-human IgG Fc antibody (CAPPEL) and protein A-HRP (ZYMED). In this case, a dilution series of commercially available human IgG1 antibody (Biogenesis) was prepared and used as a standard sample. Then, the chimeric Y9A2 antibody in the above-mentioned culture supernatant was affinity-purified using a protein A column (GE Healthcare) to give a purified chimeric Y9A2 antibody. The concentration of the purified chimeric Y9A2 antibody was calculated wherein the concentration was 1 mg/mL when the absorbance at wavelength 280 nm was 1.4.

Example 2

Cell Adhesion Inhibition Test of Chimeric Y9A2 Antibody

To compare the activity of the purified chimeric Y9A2 antibody, which was prepared by the method described in the aforementioned section, with that of a mouse Y9A2 antibody (CHEMICON INTERNATIONAL), the cell adhesion inhibition test described in J. Biol. Chem., 274: 36328-36334, 1999 was performed. To be specific, a variant (nOPN-RAA) wherein RGD sequence contained in the N terminal fragment (nOPN) resulting from cleavage of osteopontin with thrombin was substituted by RAA was first immobilized and blocked, and a mouse Y9A2 antibody or a purified chimeric Y9A2 antibody was added. Successively, SW480 cell expressing a human α9 integrin molecule (hereinafter sometimes to be indicated as SW480/hα9 cell) was added, and the mixture was incubated at 37° C. for 1 hr. Thereafter, the cell was fixed and stained with crystal violet and methanol and washed. The dye in the adhered cell was extracted with Triton X-100, and the absorbance at wavelength 595 nm was measured.

As a result, as shown in Table 1, it has been found that IC50 of the mouse Y9A2 antibody and that of the purified chimeric Y9A2 antibody are almost the same, and they have an activity to inhibit adhesion of SW480/hα9 cell to nOPN-RAA. The IC50 is defined to be a concentration of the anti-α9 integrin antibody necessary for suppressing 50% of the level of cell adhesion that occurs without addition of the anti-α9 integrin antibody.

TABLE 1

Result of cell adhesion inhibition test of mouse Y9A2 antibody and chimeric Y9A2 antibody

|  | mouse Y9A2 antibody | chimeric Y9A2 antibody |
|---|---|---|
| IC50 (µg/mL) | 0.039 | 0.038 |

Example 3

Production of Humanized Y9A2 Antibody Gene

The template human antibody to be grafted with a complementarity determining region (CDR) amino acid in VH and VL of the mouse Y9A2 antibody was selected from human antibody germlines having an amino acid sequence with high homology with framework region (FR) amino acid sequence in VH, VL of the mouse Y9A2 antibody. To be specific, template human VH selected was a combination of DP-88 and JH6 and template human VL selected was a combination of DPK-1 and JK4.

The FRs of the above-mentioned template human antibody VH and VL were grafted with the necessary amino acid sequences from VH and VL of mouse Y9A2 antibody to give a humanized antibody. To be specific, as for VH, CDR amino acid sequence and several sites of FR amino acid of the aforementioned template human antibody VH were first substituted by the corresponding amino acid sequences in VH of mouse Y9A2 antibody. The amino acid sequences of VH of two kinds of humanized Y9A2 antibodies, i.e., RY9A2VHv5 and RY9A2VHv8, were designed (SEQ ID NO: 5 and SEQ ID NO: 7, respectively), and further, the base sequences of DNAs encoding the amino acid sequences were designed (SEQ ID NO: 6 and SEQ ID NO: 8, respectively). In RY9A2VHv8, 4 of the FR amino acid residues derived from the mouse Y9A2 antibody in RY9A2VHv5 are substituted by those of the template human antibody.

As for VL, CDR amino acid sequence of the aforementioned template human antibody VL was substituted by the amino acid sequence of CDR in VL of mouse Y9A2 antibody, the amino acid sequence of RY9A2VLv01, which is VL of humanized Y9A2 antibody, was designed (SEQ ID NO: 9), and further, the base sequence of DNA encoding the amino acid sequence was designed (SEQ ID NO: 10).

To produce DNA fragments encoding the above-mentioned RY9A2VHv5, RY9A2VHv8 and RY9A2VLv01, total synthesis was performed by PCR using oligo DNA as a material. To be specific, RY9A2VHv5 was synthesized by dividing it into 6 kinds of oligo DNAs (described in SEQ ID NO: 29-34) to cover the full length of VH, as respectively shown in FIG. 3 and, using them, PCR was performed by the following procedure. That is, equivalent amounts of 6 kinds of oligo DNAs were mixed. Using the mixture as a template and Pyrobest DNA polymerase (TAKARA BIO), a step of 96° C., 30 seconds, 50° C., 30 seconds and 72° C., 3 min was repeated 15 cycles. Then, using this PCR product (1 μL) as a template, oligo DNA having the sequence indicated in bold in FIG. 3 (shown by SEQ ID NOs: 35 and 36) as a primer, and Pyrobest DNA polymerase, a step of 96° C., 20 seconds and 72° C., 2 min was repeated 25 cycles to amplify full-length VH. RY9A2VHv8 was also produced generally in the same manner.

For production of RY9A2VLv01, 15 cycles of PCR were performed in the same manner as above using six oligo DNAs (shown by SEQ ID NOs: 37-42) shown in FIG. 4 and 25 cycles of PCR were performed in the same manner as above using the amplification product as a template, and oligo DNA having the sequence indicated in bold in FIG. 4 (shown by SEQ ID NOs: 43 and 44) as a primer, whereby the full-length VL was amplified.

In both the above-mentioned VH and VL, as a leader sequence of the antibody, a sequence same as the humanized anti-osteopontin monoclonal antibody described in WO2007/139164 was used. In addition, both ends of the obtained DNA fragment were added with a HindIII recognition sequence and a BamHI recognition sequence for cloning.

The thus-obtained DNA fragments of VH and VL were digested with restriction enzymes HindIII and BamHI, ligated with the aforementioned expression vectors AG-γ1 and AG-κ, respectively, and introduced into Escherichia coli according to a conventional method for cloning. Plasmid DNA was prepared from the obtained Escherichia coli clone using a QIAprep Spin Miniprep Kit (QIAGEN). Using the obtained plasmid DNA as a template, the base sequences of the cloned VH and VL were analyzed using a GenomeLab DTCS-Quick Start Kit and CEQ2000 automatic sequencer (both by BECKMAN COULTER), whereby clones having the designed base sequences were obtained. These clones were cultured, and expression plasmids of heavy chain and light chain were purified using an EndoFree Plasmid Maxi Kit (QIAGEN).

The purified heavy chain expression plasmid and light chain expression plasmid were mixed, and the mixture was introduced into the cell to transiently express the antibody using FreeStyle 293 Expression System. In this case, a humanized Y9A2 antibody expressed by combination of a heavy chain expression plasmid inserted with RY9A2VHv5 and a light chain expression plasmid inserted with RY9A2VLv01 was named RY9A2v501 antibody, and a humanized Y9A2 antibody expressed by combination of a heavy chain expression plasmid inserted with RY9A2VHv8 and a light chain expression plasmid inserted with RY9A2VLv01 was named RY9A2v801 antibody.

Measurement of the concentration of each humanized Y9A2 antibody accumulated in the culture supernatant and acquisition of a purified antibody from the culture supernatant were performed by the same method as the aforementioned chimeric Y9A2 antibody.

Example 4

Figure 6:
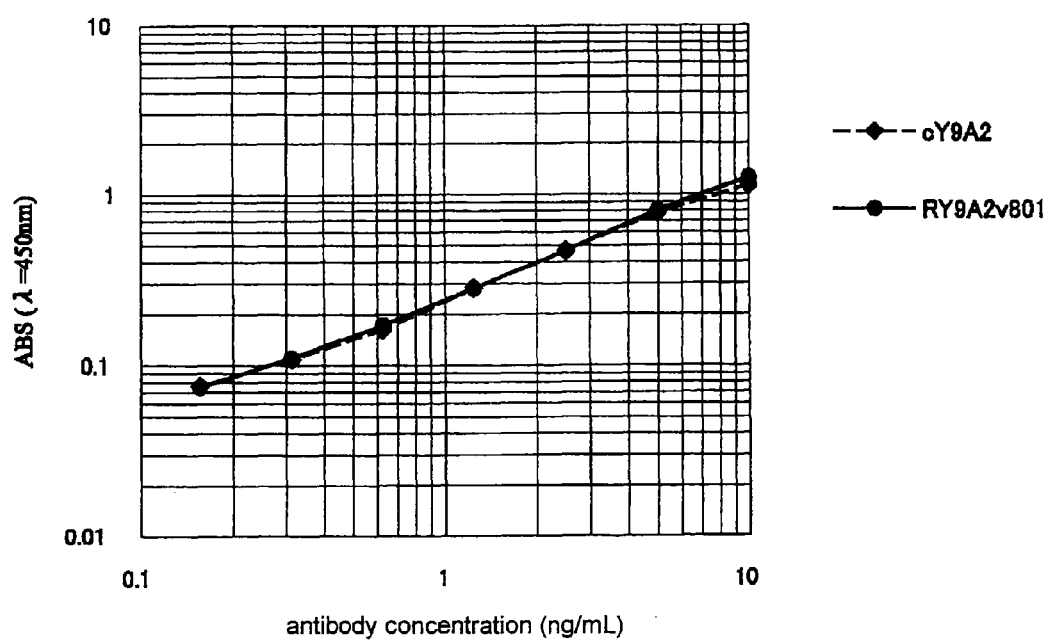
FIG. 6 shows the results of Cell ELISA of a chimeric Y9A2 antibody and an RY9A2v801 antibody.

Confirmation of Binding Activity of Humanized Y9A2 Antibody to Human α9 Integrin RY9A2v501 antibody and RY9A2v801 antibody expressed by the aforementioned method were compared with a chimeric Y9A2 antibody (hereinafter sometimes to be indicated as cY9A2 antibody) for the binding activity to human α9 integrin molecule according to a Cell ELISA method. To be specific, SW480 cells expressing human α9 integrin molecule are immobilized on an ELISA plate, reacted with the above-mentioned cY9A2 antibody or RY9A2v501 antibody or RY9A2v801 antibody, and reacted with HRP-labeled goat anti-human IgG(Fc) antibody (American Qualex) as a secondary antibody. TMB was added to allow color development, diluted sulfuric acid was added to quench the reaction and the absorbance at wavelength 450 nm was measured. As a result, as shown in FIG. 5 and FIG. 6, it has been confirmed that the RY9A2v501 antibody and the RY9A2v801 antibody have binding activity to human α9 integrin molecule equivalent to that of the cY9A2 antibody.

Example 5

Cell Adhesion Inhibition Test of Humanized Y9A2 Antibody

The above-mentioned purified RY9A2v501 antibody, purified RY9A2v801 antibody and mouse Y9A2 antibody were subjected to a cell adhesion inhibition test in the same manner as in Example 2.

The results are shown in Table 2. The IC50 (μg/mL) is defined to be a concentration of the anti-α9 integrin antibody necessary for suppressing 50% of the level of cell adhesion that occurs without addition of the anti-α9 integrin antibody. The average of the IC50 value of mouse Y9A2 antibody was 0.070 μg/mL. Table 2 shows the specific activity of humanized antibody when the IC50 value of mouse Y9A2 is 1. Table 2 shows an average value of two runs of tests. As shown in Table 2, it has been confirmed that the above-mentioned two kinds of humanized antibodies have cell adhesion inhibitory activity equivalent to that of a mouse Y9A2 antibody.

TABLE 2

Results of cell adhesion inhibition tests of mouse Y9A2 antibody, RY9A2v501 antibody and RY9A2v801 antibody

| antibody | specific activity |
|---|---|
| Y9A2 | 1.0 |
| RY9A2v501 | 0.77 |
| RY9A2v801 | 0.82 |

Example 6

Production of Improved Humanized Y9A2 Antibody

As mentioned above, since two kinds of humanized Y9A2 antibodies (RY9A2v501 antibody and RY9A2v801 antibody) having a cell adhesion inhibitory activity of the same level as the original mouse Y9A2 antibody could be acquired, the present inventors have now tried further improvement of the humanized Y9A2 antibody by introduction of mutation based on these humanized antibodies.

As a result of considerable ingenuity and consideration by the present inventors, they have succeeded in producing, as a humanized Y9A2 antibody having a significantly superior activity to that of a mouse Y9A2 antibody, the following three kinds of antibodies: RY9A2v12(M34L)012 antibody, RY9A2v11(M34L)012 antibody and RY9A2v5(IAW)01 antibody.

1. RY9A2v12(M34L)012 Antibody

The heavy chain variable region (VH) of RY9A2v12(M34L)012 antibody has the amino acid sequence shown by SEQ ID NO: 11, and the light chain variable region (VL) has the amino acid sequence shown by SEQ ID NO: 17. The base sequences of the VH and VL of the RY9A2v12(M34L)012 antibody are shown by SEQ ID NOs: 12 and 18, respectively. The VH of the RY9A2v12(M34L)012 antibody is the above-mentioned RY9A2VHv8 (SEQ ID NO: 7) wherein a methionine residue (34th amino acid residue of VH amino acid sequence) in CDR1 is substituted by leucine, as well as a lysine residue and an aspartic acid residue (65th and 66th amino acid residues of VH amino acid sequence) in CDR2 are substituted by glutamine and glycine, respectively. The VL of the RY9A2v12(M34L)012 antibody is the above-mentioned RY9A2VLv01 (SEQ ID NO: 9) wherein a lysine residue (24th amino acid residue of VL amino acid sequence) in CDR1 is substituted by arginine.

2. RY9A2v11(M34L)012 Antibody

The VH of RY9A2v11(M34L)012 antibody has the amino acid sequence shown by SEQ ID NO: 13, and VL has the amino acid sequence shown by SEQ ID NO: 17. The base sequences of VH and VL of RY9A2v11(M34L)012 antibody are shown by SEQ ID NOs: 14 and 18, respectively. The VH of the RY9A2v11(M34L)012 antibody is the above-mentioned RY9A2VHv5(SEQ ID NO: 5) wherein a methionine residue (34th amino acid residue of VH amino acid sequence) in CDR1 is substituted by leucine, as well as a lysine residue and an aspartic acid residue (65th and 66th amino acid residues of VH amino acid sequence) in CDR2 are substituted by glutamine and glycine, respectively. The VL of the RY9A2v11(M34L)012 antibody is the above-mentioned RY9A2VLv01 (SEQ ID NO: 9) wherein a lysine residue (24th amino acid residue of VL amino acid sequence) in CDR1 is substituted by arginine.

3. RY9A2v5(IAW)01 Antibody

The VH of RY9A2v5(IAW)01 antibody has the amino acid sequence shown by SEQ ID NO: 15, and VL has the amino acid sequence shown by SEQ ID NO: 9. The base sequences of VH and VL of RY9A2v5(IAW)01 are shown by SEQ ID NOs: 16 and 10, respectively. The VH of the RY9A2v5(IAW) 01 antibody is the above-mentioned RY9A2VHv5 (SEQ ID NO: 5) wherein a methionine residue (34th amino acid residue of VH amino acid sequence) in CDR1 is substituted by isoleucine, as well as an aspartic acid residue and a phenylalanine residue (104th and 105th amino acid residues of VH amino acid sequence) in CDR3 are substituted by alanine and tryptophan, respectively. The VL of RY9A2v5(IAW)01 antibody is the same as the above-mentioned RY9A2VLv01 (SEQ ID NO: 9).

The DNA fragments of VH and VL of the above-mentioned 3 kinds of improved humanized Y9A2 antibodies were ligated with the expression vectors AG-γ1 and AG-κ to give an expression plasmid in the same manner as above. The plasmid was expressed using FreeStyle 293 Expression System, and various purified antibodies were obtained from the culture supernatant by using a protein column A as mentioned above.

Example 7

Confirmation of Binding Activity of Improved Humanized Y9A2 Antibody to Human α9 Integrin The 3 kinds of humanized Y9A2 antibodies and cY9A2 antibodies produced as mentioned above were confirmed for the binding activity to human α9 integrin by CELL ELISA in the same manner as in Example 4. As a result, all of the improved humanized Y9A2 antibodies could be confirmed to have binding activity to human α9 integrin, like the chimeric Y9A2 antibody.

Example 8

Cell Adhesion Inhibition Test of Improved Humanized Y9A2 Antibody To Human nOPN

To compare the activity of the 3 kinds of improved humanized Y9A2 antibodies with that of a mouse Y9A2 antibody, the cell adhesion inhibition test was performed in the same manner as in Example 2.

The results are shown in Table 3. The IC50 (μg/mL) is defined to be a concentration of the anti-α9 integrin antibody necessary for suppressing 50% of the level of cell adhesion that occurs without addition of the anti-α9 integrin antibody. The average of IC50 values of the mouse Y9A2 antibody was 0.039 μg/mL. Table 3 shows specific activity of humanized Y9A2 antibody when the IC50 value of mouse Y9A2 is 1. The average values of 2 or 3 runs of the tests are shown in Table 3. It has been found that 3 kinds of improved humanized Y9A2 antibodies show not less than 4-fold improved cell adhesion inhibitory activity as compared to the mouse Y9A2 antibody.

TABLE 3

Results of cell adhesion inhibition test of improved humanized Y9A2 antibody

| antibody | specific activity |
| --- | --- |
| Y9A2 | 1.0 |
| RY9A2v5(IAW) 01 | 0.29 |
| RY9A2v11(M34L) 012 | 0.23 |
| RY9A2v12(M34L) 012 | 0.23 |

Example 9

Cell Adhesion Inhibition Test of Improved Humanized Y9A2 Antibody to Human VCAM-1 and Human Tenascin C The 3 kinds of improved humanized Y9A2 antibodies were examined using a ligand different from nOPN-RAA used for the aforementioned cell adhesion inhibition test. To be specific, a cell adhesion inhibitory action to human VCAM-1/Ig (R&D) and a human Tenascin C-RAA variant, wherein RGD sequence of human Tenascin C was substituted by RAA, was examined in the same manner.

Average values of two runs of tests are shown in Table 4. An average values of the cell adhesion inhibitory activity IC50 values of mouse Y9A2 antibody to human VCAM-1 and human Tenascin C-RAA were 0.077 μg/mL and 0.041 μg/mL, respectively. Table 4 shows the specific activity of humanized Y9A2 antibody when the IC50 value of mouse Y9A2 antibody is 1. It has been found that the 3 kinds of improved humanized Y9A2 antibodies show an inhibitory activity at least equivalent to that of the mouse Y9A2 antibody, though subject to variation depending on the ligand used.

TABLE 4

Results of cell adhesion inhibition test of improved humanized Y9A2 antibody to VCAM-1 and Tenascin C

| antibody | human VCAM-1 specific activity | human Tenascin C-RAA specific activity |
| --- | --- | --- |
| Y9A2 | 1.0 | 1.0 |
| RY9A2v5(IAW)01 | 1.0 | 0.44 |
| RY9A2v11(M34L)012 | 0.44 | 0.35 |
| RY9A2v12(M34L)012 | 0.95 | 0.26 |

Example 10

Cell Migration Inhibition Test of Improved Humanized Y9A2 Antibody

The 3 kinds of improved humanized Y9A2 antibodies were examined for an inhibitory action of migration activity of SW480/hα9 cell against nOPN-RAA. The experiment was based on the cell migration inhibition test described in Molecular Biology of the cell, 12: 3214-3225, 2001, with some changes made therein. To be precise, nOPN-RAA was immobilized on the upper layer of a transwell (Millipore), set on a plate, and then F15 medium containing 10% FCS was added to the lower layer. The mouse Y9A2 antibody or humanized Y9A2 antibody was added together with SW480/hα9 cell to the upper layer, and the mixture was incubated at 37° C. for 16 hr. Thereafter, the cells that migrated into the lower layer of the transwell were quantified using a QCM Chemotaxis Cell Migration 24-well Assay kit (Millipore). The migration activity inhibited by the addition of an excess amount (100 μg/mL) of the mouse Y9A2 antibody is defined as a α9-dependent migration activity (100% inhibition), and the inhibitory rate of each antibody is shown in Table 5.

A significant migration inhibitory action was found only when the mouse Y9A2 antibody was added at 50 μg/mL; however, the improved humanized Y9A2 antibody produced by the present inventors showed a significant inhibitory action at a concentration of 5 μg/mL, which is 1/10 that of the mouse Y9A2 antibody. The significant difference test was performed by Student's t-test relative to an antibody-free well. *: P<0.05, **: P<0.01.

TABLE 5

Results of cell migration inhibition test of improved humanized Y9A2 antibody

| antibody | antibody concentration (μg/mL) | inhibitory rate (%) |
| --- | --- | --- |
| Y9A2 | 5 | 28 |
|  | 20 | 24 |
|  | 50 | 99 * |
| RY9A2v5(IAW)01 | 5 | 109 ** |
| RY9A2v11(M34L)012 | 5 | 84 * |
| RY9A2v12(M34L)012 | 5 | 86 * |

The significant cell migration inhibitory action is directly linked to a clinically effective concentration, where a clinically effective concentration becoming 1/10 leads to extended administration intervals (e.g., administration of once in two weeks becomes once in several months, etc.) in clinical practice, and a blood concentration maintained at about 5 μg/mL permits development of a subcutaneous injectable preparation. Since self injection of subcutaneous injectable preparations is now permitted all over the world, the convenience in chronic diseases is strikingly improved particularly for both patients and medical institutions. Hence, improvement of biological activity by the present invention greatly contributes not only to the therapeutic effectiveness thereof but also improvement of patient compliance.

Example 11

Thermal Stability Test of Improved Humanized Y9A2 Antibody

The 3 kinds of the improved humanized Y9A2 antibodies and the mouse Y9A2 antibody were incubated at 70° C. for 2 hr or 10 hr, and evaluated for thermal stability using the cell adhesion inhibition test described in Example 8.

The average values of 4 experiments are shown in Table 6. With the cell adhesion inhibitory activity without a heat treatment as 100%, the activity residual rate of each antibody after a heat treatment is shown. Although the mouse Y9A2% antibody showed a decrease in the activity in 2 hours, the 3 kinds of the improved humanized Y9A2 antibodies retained 85% or more of the activity even after incubation for 10 hr. Hence, the property of being extremely stable to heat of the improved humanized Y9A2 antibody leads to the development of a highly convenient preparation permitting preservation at room temperature, among preparations for clinical development.

TABLE 6

Results of thermal stability test of improved humanized Y9A2 antibody

| antibody | activity residual rate (%) in 2 hr | activity residual rate (%) in 10 hr |
|---|---|---|
| Y9A2 | 27 | 33 |
| RY9A2v5(IAW)01 | 89 | 86 |
| RY9A2v11(M34L)012 | 92 | 87 |
| RY9A2v12(M34L)012 | 91 | 89 |

INDUSTRIAL APPLICABILITY

The improved humanized anti-human α9 integrin antibody of the present invention has improved activity and/or property as compared to a donor mouse anti-human α9 integrin antibody, and a strong anti-inflammatory action and a strong bone destruction suppressive action by blocking interactions between human α9 integrin and plural ligands thereof, and is useful for the prophylaxis or treatment of various diseases involving human α9 integrin in the pathogenesis.

This application is based on patent application Nos. 2008-004975 filed in Japan (filing date: Jan. 11, 2008) and 2008-282496 (filing date: Oct. 31, 2008), the contents of which are incorporated in full herein.

The invention claimed is:

1. A humanized anti-human α9 integrin antibody comprising a heavy-chain variable region consisting of the amino acid sequence shown by SEQ ID NO:11 and a light-chain variable region consisting of the amino acid sequence shown by SEQ ID NO:17.

2. The humanized anti-human α9 integrin antibody according to claim 1, wherein the heavy-chain constant region of the antibody is human Igγ1.

3. The humanized anti-human α9 integrin antibody according to claim 1, wherein the light-chain constant region of the antibody is human Igκ.

4. The humanized anti-human α9 integrin antibody according to claim 1, wherein the heavy-chain constant region of the antibody is human Igγ1 and the light-chain constant region of the antibody is human Igκ.

5. The humanized anti-human α9 integrin antibody according to claim 1, wherein the heavy chain consists of the amino acid sequence shown by SEQ ID NO:19 and the light-chain consists of the amino acid sequence shown by SEQ ID NO:25.

6. A polynucleotide comprising a sequence encoding the heavy-chain variable region of the humanized anti-human α9 integrin antibody according to claim 1.

7. A polynucleotide comprising a sequence encoding the light-chain variable region of the humanized anti-human α9 integrin antibody according to claim 1.

8. An expression vector comprising a polynucleotide comprising a sequence encoding the heavy-chain variable region of the humanized anti-human α9 integrin antibody according to claim 1 and/or a polynucleotide comprising a sequence encoding the light-chain variable region of the humanized anti-human α9 integrin antibody according to claim 1.

9. A host cell incorporating the expression vector according to claim 8.

10. A method of producing a humanized anti-human α9 integrin antibody according to claim 1, comprising a step of culturing a host cell to allow expression of the humanized anti-human α9 integrin antibody, wherein the host cell incorporates an expression vector comprising a polynucleotide comprising a sequence encoding the heavy-chain variable region of the humanized anti-human α9 integrin antibody and a polynucleotide comprising a sequence encoding the light-chain variable region of the humanized anti-human α9 integrin antibody.

11. A method of treating rheumatoid arthritis, comprising administering a therapeutically effective amount of the humanized anti-human α9 integrin antibody according to claim 1.

12. A pharmaceutical for treating rheumatoid arthritis comprising the humanized anti-human α9 integrin antibody according to claim 1.

13. A pharmaceutical composition comprising the humanized anti-human α9 integrin antibody according to claim 1 and a pharmaceutically acceptable carrier.

14. The pharmaceutical composition according to claim 13, which is in the form of an injection or drip infusion.

* * * * *

UNITED STATES PATENT AND TRADEMARK OFFICE
CERTIFICATE OF CORRECTION

| | | |
|---|---|---|
| PATENT NO. | : 8,603,476 B2 | Page 1 of 1 |
| APPLICATION NO. | : 12/812341 | |
| DATED | : December 10, 2013 | |
| INVENTOR(S) | : Uehara et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 408 days.

Signed and Sealed this
Twelfth Day of May, 2015

Michelle K. Lee
*Director of the United States Patent and Trademark Office*

UNITED STATES PATENT AND TRADEMARK OFFICE
CERTIFICATE OF CORRECTION

PATENT NO. : 8,603,476 B2  
APPLICATION NO. : 12/812341  
DATED : December 10, 2013  
INVENTOR(S) : Uehara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 415 days.

Signed and Sealed this

Twenty-third Day of May, 2017

Michelle K. Lee
*Director of the United States Patent and Trademark Office*

SEQUENCE LISTING

<160> NUMBER OF SEQ ID NOS: 46

<210> SEQ ID NO 1
<211> LENGTH: 120
<212> TYPE: PRT
<213> ORGANISM: Mus musculus

<400> SEQUENCE: 1

Gln Val Gln Leu Gln Gln Ser Gly Ala Glu Leu Ala Asn Pro Gly Ala
1               5                   10                  15

Ser Val Lys Met Ser Cys Lys Ala Ser Gly Tyr Thr Leu Thr Thr Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Thr Ser Leu Thr Ser Glu Asp Ser Ala Val Tyr Tyr Cys
                85                  90                  95

Ala Ile Tyr Gly Asp Tyr Gly Asp Phe Tyr Phe Asp Tyr Trp Gly Gln
            100                 105                 110

Gly Thr Thr Leu Thr Val Ser Ser
        115                 120

```
<210> SEQ ID NO 2
<211> LENGTH: 360
<212> TYPE: DNA
<213> ORGANISM: Mus musculus

<400> SEQUENCE: 2
caggtccagc ttcagcagtc tggggctgaa ctggcaaatc ctggggcctc agtgaagatg      60
tcctgcaagg cttctggcta cacattaact acctactgga tgcactgggt aaaacagagg     120
cctggacagg gtctggaatg gattggatac attaatccta gctctggtta tactgaatac     180
aatcagaagt tcaaggacaa ggccacgttg actgcagaca atcctccag cacagcctac      240 atgcaactga ccagcctgac atctgaggac tctgcagtct attactgtgc aatctatggt     300
gactatgggg atttctactt tgactactgg ggccagggca ccactctcac agtctcctca    360

<210> SEQ ID NO 3
<211> LENGTH: 108
<212> TYPE: PRT
<213> ORGANISM: Mus musculus

<400> SEQUENCE: 3

Ser Ile Val Met Thr Gln Thr Pro Lys Phe Leu Leu Val Ser Ala Gly
1               5                   10                  15

Asp Arg Val Thr Met Thr Cys Lys Ala Ser Gln Ser Val Asn Thr Asp
            20                  25                  30

Val Ala Trp Phe Gln Gln Lys Pro Gly Gln Ser Pro Lys Leu Leu Ile
        35                  40                  45

Tyr Phe Ala Ser Asn His Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Ile Tyr Phe Cys Arg Gln Asp Tyr Ser Ser Pro Phe
                85                  90                  95

Thr Phe Gly Gly Gly Thr Lys Leu Glu Ile Lys Arg
            100                 105

<210> SEQ ID NO 4
<211> LENGTH: 324
<212> TYPE: DNA
<213> ORGANISM: Mus musculus

<400> SEQUENCE: 4
agtattgtga tgacccagac tcccaaattc ctgcttgtat cagcaggaga cagggttacc      60
atgacctgca aggccagtca gagtgtgaat actgatgttg cttggttcca acagaagcca     120
gggcagtctc ctaaactgct gatatacttt gcatccaatc actacactgg agtccctgat     180
cgcttcactg gcagtggata tgggacggat tcacttttca ccatcagcac tgtgcaggct     240
gaagacctgg caatttattt ctgtcggcag gattacagct ctccgttcac gttcggaggg    300
gggaccaagc tggaaataaa acgg                                             324

<210> SEQ ID NO 5
<211> LENGTH: 120
<212> TYPE: PRT
<213> ORGANISM: Artificial Sequence
<220> FEATURE:
<223> OTHER INFORMATION: Description of Artificial Sequence: Synthetic
      VH chain of humanized anti-human alpha9 integrin antibody
```

-continued

<400> SEQUENCE: 5

Gln Val Gln Leu Val Gln Ser Gly Ala Glu Val Lys Lys Pro Gly Ser
1               5                   10                  15

Ser Val Lys Met Ser Cys Lys Ala Ser Gly Tyr Thr Leu Thr Thr Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Tyr Gly Asp Tyr Gly Asp Phe Tyr Phe Asp Tyr Trp Gly Gln
            100                 105                 110

Gly Thr Thr Val Thr Val Ser Ser
        115                 120

<210> SEQ ID NO 6
<211> LENGTH: 360
<212> TYPE: DNA
<213> ORGANISM: Artificial Sequence
<220> FEATURE:
<223> OTHER INFORMATION: Description of Artificial Sequence: Synthetic
      VH gene of humanized anti-human alpha9 integrin antibody

<400> SEQUENCE: 6
caggtgcagc tggtgcagtc tggggctgag gtgaagaagc ctgggtcctc cgtgaagatg      60
tcctgcaagg cttctggata caccctcacc acctactgga tgcactgggt gaaacagaga     120
cctggacaag gcttgagtg gattggatac attaatccta gctctggtta tactgaatac      180
aatcagaagt tcaaggacag agtcacgatt accgcggaca atccacgag cacagcctac      240 atggagctga gcagcctgag atctgaggac acggccgtgt attactgtgc gatttatggt     300
gactatgggg atttctactt tgactactgg gggcaaggga ccacggtcac cgtctcctca     360

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      VH chain of humanized anti-human alpha9 integrin antibody

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Leu Thr Thr Tyr
            20                  25                  30

Trp Met His Trp Val Arg Gln Ala Pro Gly Gln Gly Leu Glu Trp Met
        35                  40                  45

Gly Tyr Ile Asn Pro Ser Ser Gly Tyr Thr Glu Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Ile Tyr Gly Asp Tyr Gly Asp Phe Tyr Phe Asp Tyr Trp Gly Gln
        100                 105                 110

Gly Thr Thr Val Thr Val Ser Ser
        115                 120
```

<210> SEQ ID NO 8
<211> LENGTH: 360
<212> TYPE: DNA
<213> ORGANISM: Artificial Sequence
<220> FEATURE:
<223> OTHER INFORMATION: Description of Artificial Sequence: Synthetic
      VH gene of humanized anti-human alpha9 integrin antibody

<400> SEQUENCE: 8

```
caggtgcagc tggtgcagtc tggggctgag gtgaagaagc ctgggtcctc cgtgaaggtc    60
tcctgcaagg cttctggata caccctcacc acctactgga tgcactgggt gcgacaggcc   120
cctggacaag gcttgagtg gatgggatac attaatccta gctctggtta tactgaatac   180
aatcagaagt tcaaggacag agtcacgatt accgcgaca aatccacgag cacagcctac   240
atggagctga gcagcctgag atctgaggac acggccgtgt attactgtgc gatttatggt   300
gactatgggg atttctactt tgactactgg gggcaaggga ccacggtcac cgtctcctca   360
```

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      VL chain of humanized anti-human alpha9 integrin antibody

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asn Thr Asp
            20                  25                  30

Val Ala Trp Tyr Gln Gln Lys Pro Gly Lys Ala Pro Lys Leu Leu Ile
        35                  40                  45

Tyr Phe Ala Ser Asn His Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Arg Gln Asp Tyr Ser Ser Pro Phe
                85                  90                  95

Thr Phe Gly Gly Gly Thr Lys Val Glu Ile Lys Arg
            100                 105
```

<210> SEQ ID NO 10
<211> LENGTH: 324
<212> TYPE: DNA
<213> ORGANISM: Artificial Sequence
<220> FEATURE:
<223> OTHER INFORMATION: Description of Artificial Sequence: Synthetic
      VL gene of humanized anti-human alpha9 integrin antibody

<400> SEQUENCE: 10

```
gacatccaga tgacccagtc tccatcctcc ctgtctgcat ctgtaggaga cagagtcacc    60
atcacttgca aggccagtca gagtgtgaat actgatgttg cttggtatca gcagaaacca   120
gggaaagccc ctaagctcct gatctacttt gcatccaatc actacactgg ggtcccatca   180
aggttcagtg gaagtggatc tgggacagat tttactttca ccatcagcag cctgcagcct   240
```

```
gaagatattg caacatatta ctgtcggcag gattacagct ctccgttcac gttcggcgga    300
gggaccaagg tggagatcaa acgt                                           324
```

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      VH chain of humanized anti-human alpha9 integrin antibody

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Leu Thr Thr Tyr
            20                  25                  30

Trp Leu His Trp Val Arg Gln Ala Pro Gly Gln Gly Leu Glu Trp Met
        35                  40                  45

Gly Tyr Ile Asn Pro Ser Ser Gly Tyr Thr Glu Tyr Asn Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Tyr Gly Asp Tyr Gly Asp Phe Tyr Phe Asp Tyr Trp Gly Gln
            100                 105                 110

Gly Thr Thr Val Thr Val Ser Ser
        115                 120
```

<210> SEQ ID NO 12
<211> LENGTH: 360
<212> TYPE: DNA
<213> ORGANISM: Artificial Sequence
<220> FEATURE:
<223> OTHER INFORMATION: Description of Artificial Sequence: Synthetic
      VH gene of humanized anti-human alpha9 integrin antibody

<400> SEQUENCE: 12

```
caggtgcagc tggtgcagtc tggggctgag gtgaagaagc ctgggtcctc cgtgaaggtc    60
tcctgcaagg cttctggata caccctcacc acctactggt tgcactgggt gcgacaggcc   120
cctggacaag gcttgagtg gatgggatac attaatccta gctctggtta tactgaatac   180
aatcagaagt tccagggcag agtcacgatt accgcggaca atccacgag cacagcctac   240 atggagctga gcagcctgag atctgaggac acggccgtgt attactgtgc gatttatggt   300
gactatgggg atttctactt tgactactgg gggcaaggga ccacggtcac cgtctcctca   360
```

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      VH chain of humanized anti-human alpha9 integrin antibody

<400> SEQUENCE: 13

```
Gln Val Gln Leu Val Gln Ser Gly Ala Glu Val Lys Lys Pro Gly Ser
1               5                   10                  15

Ser Val Lys Met Ser Cys Lys Ala Ser Gly Tyr Thr Leu Thr Thr Tyr
            20                  25                  30
```

Trp Leu His Trp Val Lys Gln Arg Pro Gly Gln Gly Leu Glu Trp Ile
            35                  40                  45

Gly Tyr Ile Asn Pro Ser Ser Gly Tyr Thr Glu Tyr Asn Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Tyr Gly Asp Tyr Gly Asp Phe Tyr Phe Asp Tyr Trp Gly Gln
            100                 105                 110

Gly Thr Thr Val Thr Val Ser Ser
        115                 120

<210> SEQ ID NO 14
<211> LENGTH: 360
<212> TYPE: DNA
<213> ORGANISM: Artificial Sequence
<220> FEATURE:
<223> OTHER INFORMATION: Description of Artificial Sequence: Synthetic
      VH gene of humanized anti-human alpha9 integrin antibody

<400> SEQUENCE: 14
caggtgcagc tggtgcagtc tggggctgag gtgaagaagc ctgggtcctc cgtgaagatg      60
tcctgcaagg cttctggata caccctcacc acctactggt tgcactgggt gaaacagaga     120
cctggacaag gccttgagtg gattggatac attaatccta gctctggtta tactgaatac     180
aatcagaagt tccagggcag agtcacgatt accgcggaca atccacgag cacagcctac      240 atggagctga gcagcctgag atctgaggac acggccgtgt attactgtgc gatttatggt     300
gactatgggg atttctactt tgactactgg gggcaaggga ccacggtcac cgtctcctca     360

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      VH chain of humanized anti-human alpha9 integrin antibody

<400> SEQUENCE: 15

Gln Val Gln Leu Val Gln Ser Gly Ala Glu Val Lys Lys Pro Gly Ser
1               5                   10                  15

Ser Val Lys Met Ser Cys Lys Ala Ser Gly Tyr Thr Leu Thr Thr Tyr
            20                  25                  30

Trp Ile His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Tyr Gly Asp Tyr Gly Ala Trp Tyr Phe Asp Tyr Trp Gly Gln
            100                 105                 110

Gly Thr Thr Val Thr Val Ser Ser
        115                 120

```
<210> SEQ ID NO 16
<211> LENGTH: 360
<212> TYPE: DNA
<213> ORGANISM: Artificial Sequence
<220> FEATURE:
<223> OTHER INFORMATION: Description of Artificial Sequence: Synthetic
      VH gene of humanized anti-human alpha9 integrin antibody

<400> SEQUENCE: 16
caggtgcagc tggtgcagtc tggggctgag gtgaagaagc ctgggtcctc cgtgaagatg     60
tcctgcaagg cttctggata caccctcacc acctactgga ttcactgggt gaaacagaga    120
cctggacaag gcttgagtg gattggatac attaatccta gctctggtta tactgaatac     180
aatcagaagt tcaaggacag agtcacgatt accgcggaca atccacgag cacagcctac     240 atggagctga gcagcctgag atctgaggac acggccgtgt attactgtgc gatttatggt    300
gactatgggg cttggtactt tgactactgg gggcaaggga ccacggtcac cgtctcctca    360

<210> SEQ ID NO 17
<211> LENGTH: 108
<212> TYPE: PRT
<213> ORGANISM: Artificial Sequence
<220> FEATURE:
<223> OTHER INFORMATION: Description of Artificial Sequence: Synthetic
      VL chain of humanized anti-human alpha9 integrin antibody

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Asn Thr Asp
            20                  25                  30

Val Ala Trp Tyr Gln Gln Lys Pro Gly Lys Ala Pro Lys Leu Leu Ile
        35                  40                  45

Tyr Phe Ala Ser Asn His Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Arg Gln Asp Tyr Ser Ser Pro Phe
                85                  90                  95

Thr Phe Gly Gly Gly Thr Lys Val Glu Ile Lys Arg
            100                 105

<210> SEQ ID NO 18
<211> LENGTH: 324
<212> TYPE: DNA
<213> ORGANISM: Artificial Sequence
<220> FEATURE:
<223> OTHER INFORMATION: Description of Artificial Sequence: Synthetic
      VL gene of humanized anti-human alpha9 integrin antibody

<400> SEQUENCE: 18
gacatccaga tgacccagtc tccatcctcc ctgtctgcat ctgtaggaga cagagtcacc     60
atcacttgca gggccagtca gagtgtgaat actgatgttg cttggtatca gcagaaacca    120
gggaaagccc ctaagctcct gatctacttt gcatccaatc actacactgg ggtcccatca    180
aggttcagtg gaagtggatc tgggacagat tttactttca ccatcagcag cctgcagcct    240
gaagatattg caacatatta ctgtcggcag gattacagct ctccgttcac gttcggcgga    300
gggaccaagg tggagatcaa acgt                                            324
```

<210> SEQ ID NO 19
<211> LENGTH: 450
<212> TYPE: PRT
<213> ORGANISM: Artificial Sequence
<220> FEATURE:
<223> OTHER INFORMATION: Description of Artificial Sequence: Synthetic
      H chain of humanized anti - human alpha9 integrin antibody

<400> SEQUENCE: 19

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Leu Thr Thr Tyr
            20                  25                  30

Trp Leu His Trp Val Arg Gln Ala Pro Gly Gln Gly Leu Glu Trp Met
        35                  40                  45

Gly Tyr Ile Asn Pro Ser Ser Gly Tyr Thr Glu Tyr Asn Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Tyr Gly Asp Tyr Gly Asp Phe Tyr Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 20
<211> LENGTH: 1350
<212> TYPE: DNA
<213> ORGANISM: Artificial Sequence
<220> FEATURE:
<223> OTHER INFORMATION: Description of Artificial Sequence: Synthetic
      H gene of humanized anti - human alpha9 integrin antibody

<400> SEQUENCE: 20
caggtgcagc tggtgcagtc tggggctgag gtgaagaagc ctgggtcctc cgtgaaggtc      60
tcctgcaagg cttctggata caccctcacc acctactggt tgcactgggt gcgacaggcc    120
cctggacaag gcttgagtg gatgggatac attaatccta gctctggtta tactgaatac    180
aatcagaagt tccagggcag agtcacgatt accgcggaca atccacgag cacagcctac    240
atggagctga gcagcctgag atctgaggac acggccgtgt attactgtgc gatttatggt    300
gactatgggg atttctactt tgactactgg ggccaaggga ccacggtcac cgtctcctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350

<210> SEQ ID NO 21
<211> LENGTH: 450
<212> TYPE: PRT
<213> ORGANISM: Artificial Sequence
```

-continued

```
<220> FEATURE:
<223> OTHER INFORMATION: Description of Artificial Sequence: Synthetic
      H chain of humanized anti - human alpha9 integrin antibody

<400> SEQUENCE: 21
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 |
| Ser | Val | Lys | Met | Ser | Cys | Lys | Ala | Ser | Gly | Tyr | Thr | Leu | Thr | Thr | Tyr |
| | | | 20 | | | | | 25 | | | | | 30 | | |
| Trp | Leu | His | Trp | Val | Lys | Gln | Arg | Pro | Gly | Gln | Gly | Leu | Glu | Trp | Ile |
| | | 35 | | | | | 40 | | | | | 45 | | | |
| Gly | Tyr | Ile | Asn | Pro | Ser | Ser | Gly | Tyr | Thr | Glu | Tyr | Asn | Gln | Lys | Phe |
| | 50 | | | | | 55 | | | | | 60 | | | | |
| Gln | Gly | Arg | Val | Thr | Ile | Thr | Ala | Asp | Lys | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Ile | Tyr | Gly | Asp | Tyr | Gly | Asp | Phe | Tyr | Phe | Asp | Tyr | Trp | Gly | Gln |
| | | | 100 | | | | | 105 | | | | | 110 | | |
| Gly | Thr | Thr | Val | Thr | Val | Ser | Ser | Ala | Ser | Thr | Lys | Gly | Pro | Ser | Val |
| | | | 115 | | | | | 120 | | | | | 125 | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Lys | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | 325 | | | | | 330 | | | | | 335 | | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Asp | Glu | Leu | Thr | Lys | Asn | Gln | Val | Ser | Leu |
| | | 355 | | | | | 360 | | | | | 365 | | | |
| Thr | Cys | Leu | Val | Lys | Gly | Phe | Tyr | Pro | Ser | Asp | Ile | Ala | Val | Glu | Trp |
| | | 370 | | | | | 375 | | | | | 380 | | | |
| Glu | Ser | Asn | Gly | Gln | Pro | Glu | Asn | Asn | Tyr | Lys | Thr | Thr | Pro | Pro | Val |
| 385 | | | | | 390 | | | | | 395 | | | | | 400 |

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 22
<211> LENGTH: 1350
<212> TYPE: DNA
<213> ORGANISM: Artificial Sequence
<220> FEATURE:
<223> OTHER INFORMATION: Description of Artificial Sequence: Synthetic
      H gene of humanized anti - human alpha9 integrin antibody

<400> SEQUENCE: 22
caggtgcagc tggtgcagtc tggggctgag gtgaagaagc ctgggtcctc cgtgaagatg      60
tcctgcaagg cttctggata caccctcacc acctactggt tgcactgggt gaaacagaga     120
cctggacaag gcttgagtg gattggatac attaatccta gctctggtta tactgaatac     180
aatcagaagt tccagggcag agtcacgatt accgcggaca atccacgag cacagcctac      240 atggagctga gcagcctgag atctgaggac acggccgtgt attactgtgc gatttatggt     300
gactatgggg atttctactt tgactactgg gggcaaggga ccacggtcac cgtctcctca     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggggga    720 ccgtcagtct tcctcttccc cccaaaaccc aaggacaccc tcatgatctc ccggaccccctt   780 gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggatgag     1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                     1350

<210> SEQ ID NO 23
<211> LENGTH: 450
<212> TYPE: PRT
<213> ORGANISM: Artificial Sequence
<220> FEATURE:
<223> OTHER INFORMATION: Description of Artificial Sequence: Synthetic
      H chain of humanized anti - human alpha9 integrin antibody

<400> SEQUENCE: 23

```
Gln Val Gln Leu Val Gln Ser Gly Ala Glu Val Lys Lys Pro Gly Ser
1               5                   10                  15

Ser Val Lys Met Ser Cys Lys Ala Ser Gly Tyr Thr Leu Thr Thr Tyr
            20                  25                  30

Trp Ile His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Tyr Gly Asp Tyr Gly Ala Trp Tyr Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 24
<211> LENGTH: 1350
<212> TYPE: DNA
<213> ORGANISM: Artificial Sequence
<220> FEATURE:
<223> OTHER INFORMATION: Description of Artificial Sequence: Synthetic
      H gene of humanized anti - human alpha9 integrin antibody

<400> SEQUENCE: 24
```

| | |
|---|---|
| caggtgcagc tggtgcagtc tggggctgag gtgaagaagc ctgggtcctc cgtgaagatg | 60 |
| tcctgcaagg cttctggata caccctcacc acctactgga ttcactgggt gaaacagaga | 120 |
| cctggacaag gcttgagtg gattggatac attaatccta gctctggtta tactgaatac | 180 |
| aatcagaagt tcaaggacag agtcacgatt accgcggaca atccacgag cacagcctac | 240 |
| atggagctga gcagcctgag atctgaggac acggccgtgt attactgtgc gatttatggt | 300 |
| gactatgggg cttggtactt tgactactgg ggcaaggga ccacggtcac cgtctcctca | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaaaactca cacatgccca ccgtgcccag cacctgaact cctggggga | 720 |
| ccgtcagtct tcctcttccc cccaaaaccc aaggacaccc tcatgatctc ccggaccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag gcagccccg agaaccacag gtgtacaccc tgcccccatc ccgggatgag | 1080 |
| ctgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctac agcaagctca ccgtggacaa gagcaggtgg | 1260 |
| cagcaggga acgtcttctc atgctccgtg atgcatgagg ctctgcacaa ccactacacg | 1320 |
| cagaagagcc tctccctgtc tccgggtaaa | 1350 |

```
<210> SEQ ID NO 25
<211> LENGTH: 214
<212> TYPE: PRT
<213> ORGANISM: Artificial Sequence
<220> FEATURE:
<223> OTHER INFORMATION: Description of Artificial Sequence: Synthetic
      L chain of humanized anti - human alpha9 integrin antibody
```

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Asn Thr Asp
            20                  25                  30

Val Ala Trp Tyr Gln Gln Lys Pro Gly Lys Ala Pro Lys Leu Leu Ile
        35                  40                  45

Tyr Phe Ala Ser Asn His Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Arg Gln Asp Tyr Ser Ser Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 642
<212> TYPE: DNA
<213> ORGANISM: Artificial Sequence
<220> FEATURE:
<223> OTHER INFORMATION: Description of Artificial Sequence: Synthetic
      L gene of humanized anti - human alpha9 integrin antibody

<400> SEQUENCE: 26
gacatccaga tgacccagtc tccatcctcc ctgtctgcat ctgtaggaga cagagtcacc      60
atcacttgca gggccagtca gagtgtgaat actgatgttg cttggtatca gcagaaacca     120
gggaaagccc ctaagctcct gatctacttt gcatccaatc actacactgg ggtcccatca     180
aggttcagtg gaagtggatc tgggacagat tttactttca ccatcagcag cctgcagcct     240
gaagatattg caacatatta ctgtcggcag gattacagct ctccgttcac gttcggcgga     300
gggaccaagg tggagatcaa acgtactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                       642

<210> SEQ ID NO 27
<211> LENGTH: 214
<212> TYPE: PRT
<213> ORGANISM: Artificial Sequence
<220> FEATURE:
<223> OTHER INFORMATION: Description of Artificial Sequence: Synthetic
      L chain of humanized anti - human alpha9 integrin antibody

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asn Thr Asp
            20                  25                  30

Val Ala Trp Tyr Gln Gln Lys Pro Gly Lys Ala Pro Lys Leu Leu Ile
        35                  40                  45

Tyr Phe Ala Ser Asn His Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Arg Gln Asp Tyr Ser Ser Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 642
<212> TYPE: DNA
<213> ORGANISM: Artificial Sequence
<220> FEATURE:
<223> OTHER INFORMATION: Description of Artificial Sequence: Synthetic
      L gene of humanized anti - human alpha9 integrin antibody

<400> SEQUENCE: 28
gacatccaga tgacccagtc tccatcctcc ctgtctgcat ctgtaggaga cagagtcacc      60
atcacttgca aggccagtca gagtgtgaat actgatgttg cttggtatca gcagaaacca     120
gggaaagccc ctaagctcct gatctacttt gcatccaatc actacactgg ggtcccatca     180
aggttcagtg gaagtggatc tgggacagat tttactttca ccatcagcag cctgcagcct     240
gaagatattg caacatatta ctgtcggcag gattacagct ctccgttcac gttcggcgga     300
gggaccaagg tggagatcaa acgtactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540

```
ctgagcaaag cagactacga gaaacacaaa gtctacgcct gcgaagtcac ccatcagggc      600
ctgagctcgc ccgtcacaaa gagcttcaac aggggagagt gt                        642
```

<210> SEQ ID NO 29
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
cagcaagctt gccgccacca tggaatggag ctggatcttt ctcttcctcc tgtcagtaac      60
tgcaggtgtc caatcccagg tgcagctggt gc                                   92
```

<210> SEQ ID NO 30
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
aggcttctgg atacaccctc accacctact ggatgcactg ggtgaaacag agacctggac      60
aagggcttga gtggattgga tacattaatc ctagct                               96
```

<210> SEQ ID NO 31
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

```
ggacaaatcc acgagcacag cctacatgga gctgagcagc ctgagatctg aggacacggc      60
cgtgtattac tgtgcgattt atggtgacta tgg                                  93
```

<210> SEQ ID NO 32
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

```
tcgcggatcc actcacctga ggagacggtg accgtggtcc cttgccccca gtagtcaaag      60
tagaaatccc catagtcacc ataaatcgca cag                                  93
```

<210> SEQ ID NO 33
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

```
ggtgagggtg tatccagaag ccttgcagga catcttcacg gaggacccag gcttcttcac      60
ctcagcccca gactgcacca gctgcacctg ggatt                                95
```

-continued

```
<210> SEQ ID NO 34
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gctgtgctcg tggatttgtc cgcggtaatc gtgactctgt ccttgaactt ctgattgtat    60
tcagtataac cagagctagg attaatgtat ccaatcc                             97

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cagcaagctt gccgccacca tggaatggag ctggatcttt                          40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcgcggatcc actcacctga ggagacggtg accgtggtcc                          40

<210> SEQ ID NO 37
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cagcaagctt gccgccacca tgaagttgcc tgttaggctg ttggtgctga tgttctggat    60
tcctgcttcc agcagtgaca tccagatgac cca                                 93

<210> SEQ ID NO 38
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tattcacact ctgactggcc ttgcaagtga tggtgactct gtctcctaca gatgcagaca    60
gggaggatgg agactgggtc atctggatgt cactg                               95

<210> SEQ ID NO 39
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 39
aggccagtca gagtgtgaat actgatgttg cttggtatca gcagaaacca gggaaagccc    60
ctaagctcct gatctacttt gcatccaatc ac                                 92

<210> SEQ ID NO 40
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tgctgatggt gaaagtaaaa tctgtcccag atccacttcc actgaacctt gatgggaccc    60
cagtgtagtg attggatgca agtagatca g                                   91

<210> SEQ ID NO 41
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cagattttac tttcaccatc agcagcctgc agcctgaaga tattgcaaca tattactgtc    60
ggcaggatta cagctctccg ttcacgtt                                      88

<210> SEQ ID NO 42
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcgcggatcc aactgaggaa gcaaagttta aattctactc acgtttgatc tccaccttgg    60
tccctccgcc gaacgtgaac ggagagctgt aa                                 92

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cagcaagctt gccgccacca tgaagttgcc tgttaggctg                          40

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcgcggatcc aactgaggaa gcaaagttta aattctactc                          40
```

```
<210> SEQ ID NO 45
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Glu Trp Ser Trp Ile Phe Leu Phe Leu Leu Ser Val Thr Ala Gly
1               5                   10                  15

Val Gln Ser Gln Val Gln Leu Val Gln Ser Gly Ala Glu Val Lys Lys
            20                  25                  30

Pro Gly Ser Ser Val Lys Met Ser Cys Lys Ala Ser Gly Tyr Thr Leu
        35                  40                  45

Thr Thr Tyr Trp Met His Trp Val Lys Gln Arg Pro Gly Gln Gly Leu
    50                  55                  60

Glu Trp Ile Gly Tyr Ile Asn Pro Ser Ser Gly Tyr Thr Glu Tyr Asn
65                  70                  75                  80

Gln Lys Phe Lys Asp Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Ile Tyr Gly Asp Tyr Gly Asp Phe Tyr Phe Asp Tyr
        115                 120                 125

Trp Gly Gln Gly Thr Thr Val Thr Val Ser Ser
    130                 135

<210> SEQ ID NO 46
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Lys Leu Pro Val Arg Leu Leu Val Leu Met Phe Trp Ile Pro Ala
1               5                   10                  15

Ser Ser Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Ser Val
        35                  40                  45

Asn Thr Asp Val Ala Trp Tyr Gln Gln Lys Pro Gly Lys Ala Pro Lys
    50                  55                  60

Leu Leu Ile Tyr Phe Ala Ser Asn His Tyr Thr Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Arg Gln Asp Tyr Ser
            100                 105                 110

Ser Pro Phe Thr Phe Gly Gly Gly Thr Lys Val Glu Ile Lys Arg
        115                 120                 125
```